(12) United States Patent
Törnqvist et al.

(10) Patent No.: US 9,320,768 B2
(45) Date of Patent: Apr. 26, 2016

(54) COMPOSITION FOR TREATMENT OF NEURODEGENERATIVE DISEASES OR DISORDERS, METHOD AND USE COMPRISING ELECTROMAGNETICALLY IRRADIATED YEAST

(75) Inventors: Kent Törnqvist, Rodeby (SE); Maria Sibileva, Rodeby (SE); Peter Ek, Färjestaden (SE); Anders Fredriksson, Uppsala (SE); Trevor Archer, Floda (SE); Tatiana Blomqvist, Trekranten (SE); Dmitry Mudrik, Fryazino (RU); Natalia Golant, Fryazino (RU); Ludmila Balakireva, Schelkovo (RU)

(73) Assignee: Milmed AB, Färjestaden (SE)

( * ) Notice: Subject to any disclaimer, the term of this patent is extended or adjusted under 35 U.S.C. 154(b) by 799 days.

(21) Appl. No.: 13/390,643

(22) PCT Filed: Aug. 26, 2010

(86) PCT No.: PCT/EP2010/062490
§ 371 (c)(1),
(2), (4) Date: Apr. 11, 2012

(87) PCT Pub. No.: WO2011/023769
PCT Pub. Date: Mar. 3, 2011

(65) Prior Publication Data
US 2012/0190095 A1      Jul. 26, 2012

(30) Foreign Application Priority Data
Aug. 26, 2009  (SE) .................................. 0950613

(51) Int. Cl.
*A61K 36/064* (2006.01)
*A61K 41/00* (2006.01)
(52) U.S. Cl.
CPC ............... *A61K 36/064* (2013.01); *A61K 41/00* (2013.01)

(58) Field of Classification Search
None
See application file for complete search history.

(56) References Cited

FOREIGN PATENT DOCUMENTS

| EA | 004756 B1 | 8/2004 |
|---|---|---|
| EP | 1374877 A1 | 1/2004 |
| EP | 1375653 A1 | 1/2004 |
| EP | 1774972 A1 * | 4/2007 |
| SU | 1564189 A * | 5/1990 |
| WO | WO-02/062982 A1 | 8/2002 |
| WO | WO-02/062983 A1 | 8/2002 |
| WO | WO-02/062984 A1 | 8/2002 |

OTHER PUBLICATIONS

Derwent Abstract for SU 1564189. May 15, 1990.*
English translation of SU 1564189. May 15, 1990.*
Derwent abstract of WO 02/62982. Aug. 15, 2002.*
International Search Report in International Application No. PCT/EP2010/062490, filed Aug. 26, 2010.
Novaroli, L. et al. "Human recombinant monoamine oxidase B as reliable and efficient enzyme source for inhibitor screening" *Bioorganic & Medicinal Chemistry*, 2005, 13:6212-6217.
Rojavin, M.A. et al. "Medical application of millimetre waves" *Quarterly Journal of Medicine*, 1998, 91:57-66.

* cited by examiner

*Primary Examiner* — Renee Claytor
*Assistant Examiner* — Susan E Fernandez
(74) *Attorney, Agent, or Firm* — Saliwanchik, Lloyd & Eisenschenk

(57) ABSTRACT

Provided is a composition which comprises yeast cells treated with, or grown from yeast cells treated with electromagnetic waves in the range of 30 GHz to 300 GHz. Said composition may be used for the treatment of neurodegenerative diseases or disorders. A method relating to the composition is also provided.

8 Claims, 13 Drawing Sheets

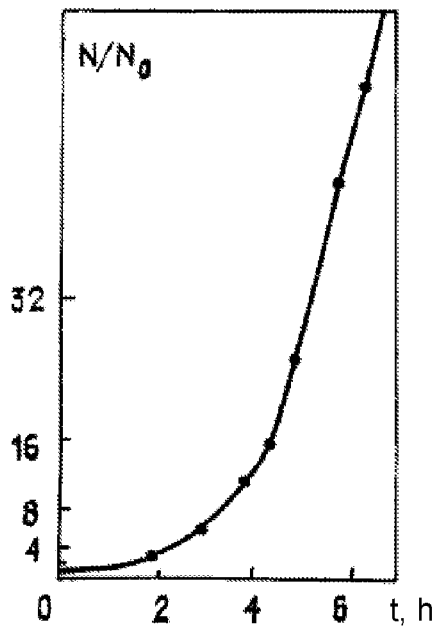
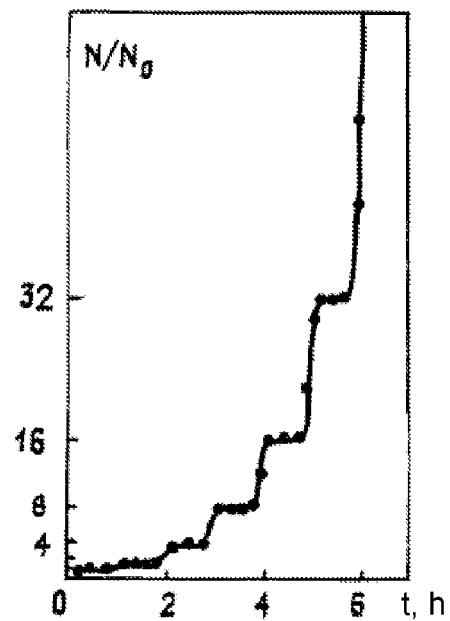
Fig. 1A
Fig. 1B
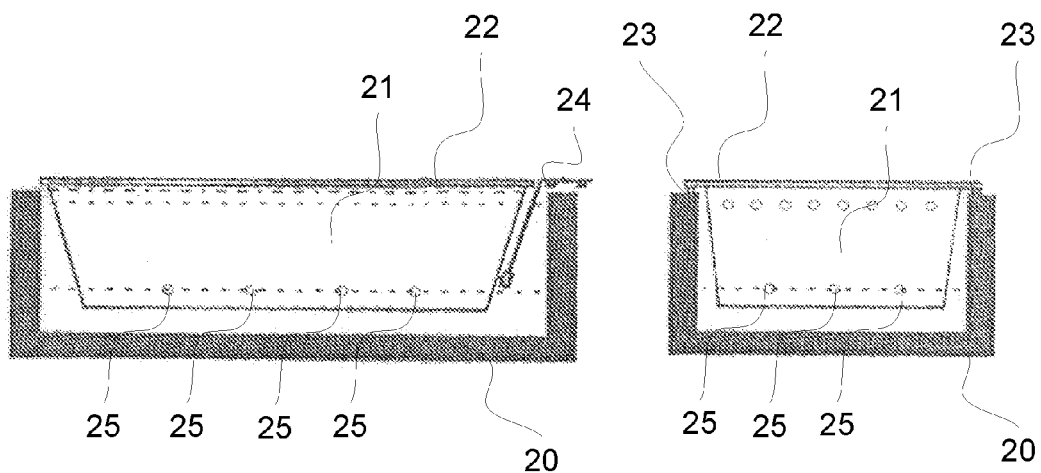
Fig. 2 A
Fig. 2 B

COMPOSITION FOR TREATMENT OF NEURODEGENERATIVE DISEASES OR DISORDERS, METHOD AND USE COMPRISING ELECTROMAGNETICALLY IRRADIATED YEAST

CROSS-REFERENCE TO RELATED APPLICATIONS

This application is the U.S. national stage application of International Patent Application No. PCT/EP2010/062490, filed Aug. 26, 2010, which claims priority to European Application No. 0950613-0, filed Aug. 26, 2009, the disclosures of each of which are incorporated herein by reference in their entirety.

TECHNICAL FIELD

The present invention relates to a composition for treatment of neurodegenerative diseases or disorders, use of such composition as well as a method for producing such composition.

BACKGROUND

Neurodegenerative diseases or disorders are conditions in which cells of the brain and spinal cord are lost. The brain and spinal cord are composed of neurons that perform different functions. Such functions may be controlling movements, processing sensory information, or making decisions. Cells of the brain and spinal cord are not readily regenerated, so excessive damage can be irreversible. Neurodegenerative diseases result from deterioration of neurons or their myelin sheath which over time will lead to dysfunction or different kinds of diseases or disorders.

Apoptosis is a phenomenon that comes to pass in neural tissue to stop injured cells from harming intact cells in the organism, during the development of the nervous system. During apoptosis cells undertake a series of morphological changes, which comprise cell shrinkage, chromatin condensation, DNA fragmentation, etc. Dysfunctional control of apoptosis causes extreme cell deaths, for example in Parkinson's disease and Alzheimer's disease.

Initial treatment of neurodegenerative diseases or disorders is dependent on diagnosis and progression of the specific disease or disorder. At present there are few therapies known within the art for the wide range of neurodegenerative diseases or disorders that exist.

For Parkinson's disease, treatment with L-dihydroxy-phenyl-alanine (L-dopa; levodopa) can inhibit symptoms for a short time, but then causes acceleration of the symptoms. Efforts are also being made to develop therapies for Alzheimer's disease that will stabilize cognitive function at the level existing at time of initial diagnosis. Similarly, other neurodegenerative diseases or disorders, such as amylotrophic lateral sclerosis (ALS) or conditions related to Diabetes Mellitus type 2. However, these therapies often have limited effect, are expensive and may be associated with serious side effects. They are also not preventive.

Thus, there is a need for new methods and compositions allowing for improved treatment or prevention of neurodegenerative diseases or disorders.

SUMMARY

Accordingly, the present invention seeks to mitigate, alleviate or eliminate one or more of the above-identified deficiencies and to provide improved treatment of the kind referred to, and specifically compositions used therein.

For this purpose, in a first aspect, a composition comprising yeast cells treated with, or grown from yeast cells treated with electromagnetic waves in the range of 30 GHz to 300 GHz, for the treatment or prevention of neurodegenerative diseases or disorders is provided.

An advantage with the inventive composition is that it allows for improved and cost-effective treatment of neurodegenerative diseases or disorders.

In a second aspect, a method for preparing a composition according to the first aspect is provided. Said method comprise the steps of preparing a growth medium, sterilizing or pasteurizing said growth medium, growing yeast cells in said growth medium and treating said yeast cells with electromagnetic waves, wherein said electromagnetic waves are in the range of 30 GHz to 300 GHz.

Further advantageous features of the invention and its embodiments are defined in the appended claims and in the detailed description.

BRIEF DESCRIPTION OF DRAWINGS

These and other aspects, features and advantages of which the invention is capable, will be apparent from the following description of illustrative embodiments of the present invention, reference being made to the accompanying drawings, in which FIG. 1A is a diagram showing a growth curve of untreated yeast cells and FIG. 1B is a diagram showing a growth curve of treated cells according to an embodiment;

FIG. 2 discloses an illustration of an experimental apparatus. FIG. 2A is a side view and FIG. 2B is a front view;

DETAILED DESCRIPTION

Figure 3:
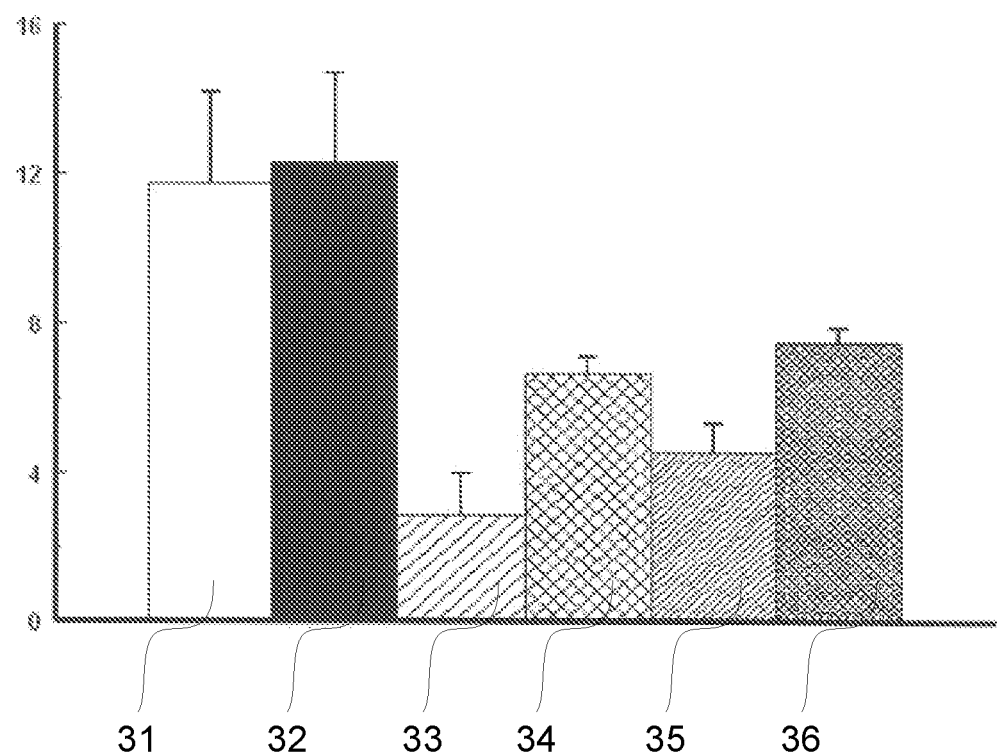
FIG. 3 is a diagram showing the DA content in striatum of mice used to test the invention.

The use of low-intensity electromagnetic millimeter waves within non-traditional areas, such as medicine, biology and biotechnology is a trend that originated in Russia in the middle of the 1960s as a result of pioneering work made by M. B. Golant et al. The millimeter waves are electromagnetic waves with extreme high frequency, so called EHF-waves. The frequency is in the range of about 30 GHz to about 300 GHz. These waves are greatly absorbed by water and other aqueous media, and have various effects on biological organisms. The penetration depth of EHF radiation in tissue is only fractions of a millimeter. At the same time, direct experiments with living organisms indicated that EHF impact on the surface of a living body also influences tissue located on a distance from the site exposed to radiation.

There are several experimental investigations, which indicate the influence of low-intensity millimeter waves on chemical, biochemical and metabolic processes in cells and model systems. For example, millimeter waves have been shown to accelerate active transport of $Na^+$-ions, to influence conductivity of lipid membranes and to stimulate synthesis of ATP in the cell. Waves in the EHF range are believed to be the main instrument used by self-regulatory systems of organisms to recover disturbed functions and maintain homeostasis. In Russia, more than 2 000 000 patients have been treated with EHF therapy and it has been shown to be effective against diseases and symptoms in for example the gastrointestinal tract. Furthermore, EHF therapy can be used as a complement to treatments with drugs and other kinds of radiation, since it reduces stress and relieves pain.

EHF waves are facilitated by resonance circuits formed by long-lasting protein structures in connection with cell membranes. This facilitation occurs at the expense of energy, which is taken from the cell metabolism.

The cell membrane is a lipid bi-layer comprising proteins. It is also polarized, which means that there is an electric potential between the outer and inner surfaces of the membrane. Various deviations from the normal cell functions are always accompanied by the appearance of an electrical asymmetry in the cell membrane. Acoustic waves propagating along membranes cause periodical changes in membrane thickness determined by the Poisson factor. The spatial period of changes in membrane thickness is equal to the acoustic wavelength. In polarized dielectric membranes such changes of thickness are accompanied by changes in the electric field, with the same period in time and space as acoustic waves. These waves in the cell membrane are thus called acoustic-electric waves.

Living organisms produce EHF signals themselves, in their membranes. However, in cells with symmetric electric distribution and normal functions, there are no reasons for generation of particular resonance frequencies. But if these signals occur, they can be sent through the cellular mass of an organism, extending the effect of the external radiation. EHF radiation is used for recovery by the organism itself. This recovery is organized exceptionally by the perfect cybernetic system, which manages the processes of recovery and maintenance of organism's homeostasis. Informational systems of all cells, organs and systems of the organism take part in the functioning of this system and recovery processes in all elements of the organism are controlled by their own signals reflecting peculiarities of occurred disturbances.

Resonance waves in cells also arise from external EHF radiation. The external EHF radiation can thus be transformed into resonance waves, internal EHF waves, produced by the cells themselves, for the purpose of recovery. The cells themselves can accomplish restoration of electric symmetry without external EHF stimulation. However, if the cells are depressed in any way the natural restoration might be slow or never take place. In these cases EHF radiation can be used for acceleration of the restoration. This is the reason for treatment by EHF radiation, but since it would be impossible to develop a precise set of signals with the help of an external technical device one can induce the internal EHF waves. Humans, for example, consist of as much as $10^{13}$ cells, each with a potential to generate an individual signal system, which would be impossible to regenerate. If, however, cells are treated with external signals, the informational systems of cells, organs and functions of the organism transforms these signals into coherent internal EHF acoustic-electric waves that corresponds the natural mechanisms of own recovery in these cells.

Thanks to such transformation external EHF radiation contributes to formation of signals necessary for the recovery of an organism. Restoration of the electric symmetry in a membrane results in termination of the mechanisms generating the acoustic-electric waves. As a result, temporary protein substructures appearing in the cell membranes gradually dissolve after functions get normalized.

There are more than thousand various types of protein molecules in cells whose resonance frequency bands overlap the EHF band. Dipolar oscillations of such molecules cause EHF waves at the expense energy drawn from cell metabolism. The proteins have been shown to form conglomerates in membrane regions where the electric disturbance is large. Thus, proteins located over a membrane surface can provide oscillations of amplitudes creating acoustic-electric waves.

Furthermore, since the waves cannot propagate through free space, the conglomerates in which oscillations are in phase with each other work as an antenna lattice sending the signal to neighbouring cells. Thus, the mechanisms triggered by EHF radiation in living organisms seems to be based on the synchronization of intercellular as well as intracellular recovery processes due to the stimulation of coherent EHF oscillations, i.e. the effect of EHF radiation increases resistance in a multicellular system. Cells, which circulate in blood and lymph systems in for example a human body, can further propagate the EHF waves, since they constantly exchange EHF oscillations with the neighbours.

It has surprisingly been found that a composition comprising yeast cells treated with, or grown from yeast cells treated with, or grown from yeast cells treated with, electromagnetic waves in the range of 30 GHz to 300 GHz (so called treated yeast cells or treated yeast) are effective for the treatment or prevention of neurodegenerative diseases or disorders. An advantage with said composition is that it allows for improved and cost-effective treatment of neurodegenerative diseases or disorders.

The electromagnetic waves may be delivered with any electronic or photonic device known within the art. The electromagnetic waves may have a power density below 1 mW/cm$^2$, such as about 0.1 mW/cm$^2$.

In an embodiment, the oscillation frequency is within the range from about 35 to about 65 GHz. The electromagnetic waves may be delivered with any electronic or photonic device known within the art. The electromagnetic waves may have a power density below 1 mW/cm$^2$, such as about 0.1 mW/cm$^2$.

In an embodiment, the oscillation frequency is chosen from the group consisting of 40 GHz, 41 GHz, 42 GHz, 43 GHz, 44 GHz, 45 GHz, 46 GHz, 47 GHz, 48 GHz, 49 GHz, 50 GHz, 51 GHz, 52 GHz, 53 GHz, 54 GHz, or 55 GHz. The electromagnetic waves may be delivered with any electronic or photonic device known within the art. The electromagnetic waves may have a power density below 1 mW/cm$^2$, such as about 0.1 mW/cm$^2$. In an embodiment, the oscillation frequency is 42194±10 MHz and linearly modulated within a 100 MHz band around this frequency. The electromagnetic waves may be delivered with any electronic or photonic device known within the art. The electromagnetic waves may have a power density below 1 mW/cm$^2$, such as about 0.1 mW/cm$^2$. In an embodiment, the oscillation frequency is 53534±10 MHz and linearly modulated within a 50 MHz band around this frequency. The electromagnetic waves may be delivered with any electronic or photonic device known within the art. The electromagnetic waves may have a power density below 1 mW/cm$^2$, such as about 0.1 mW/cm$^2$.

In an embodiment, said yeast cells are *Sacharomyces*, such as selected from the group comprising *Sacharomyces carlsbergesis* or *Sacharomyces cerevisiae*. An advantage with this is that such yeast may be readily available at a low cost.

Neurodegenerative diseases or disorders are in general caused by an ongoing loss of nerve cells, more or less selectively. With disease progression, there may be an acceleration of the ongoing loss of nerve cells.

According to the principle of plasticity every nerve cell has the ability to self repair, given the right conditions. Such conditions may be somatic or life style factors. It is for example well known within the art that physical exercise may help slow the progression of neurodegenerative diseases or disorders.

In general, physical exercise has been shown to have a substantial role in stimulating trophic factors in the nerve tissue, so called neurotrophic factors. One such factor is Brain-derived neurotrophic factor (BDNF). It has been shown that physical exercise increases the levels of BDNF. It is hypothesised, according to a non-limiting theory of the inventors, that treated yeast cells in combination with physical exercise induce a hyper-stimulation which increases further levels of BDNF. Increased levels of BDNF may then serve as a basis for the mobilisation of restoration and repair of nerve tissue. Increased plasticity due to combining physical exercise and the yeast compound is hypothesised to provide a synergism that reduces the progression of the neurodegenerative condition.

It has been shown that levels of BDNF specifically affect the progression of a number of neurodegenerative conditions, such as Parkinson's disease, Alzheimer's disease and ALS. The neurodegenerative effects of Diabetes Mellitus type 2 may also be affected by imbalances in BDNF.

In an embodiment, the neurodegenerative disease or disorder is Parkinson's disease.

In an embodiment, the neurodegenerative disease or disorder is Alzheimer's disease.

In an embodiment, the neurodegenerative disease or disorder is amyotrophic lateral sclerosis (ALS).

In an embodiment, the neurodegenerative disease or disorder is Diabetes Mellitus type 2.

In an embodiment, the treatment is oral treatment, e.g. in the form of a malt beverage or in any kind of beverage comprising the treated yeast.

The treated yeast may otherwise be distributed to the subject in any form suitable. The subject may be any mammal, such as e.g. humans. EHF energy is thus transferred into the treated subject in form of treated yeast externally stimulated by EHF radiation.

In an aspect, the composition is obtainable by a method comprising the steps: preparing a growth medium; sterilizing or pasteurizing the growth medium; growing yeast cells in the growth medium; and treating the yeast with electromagnetic waves, wherein the electromagnetic waves is in the range of 30 GHz to 300 GHz.

In an embodiment, the electromagnetic waves is within the range from about 35 to about 65 GHz, such as 40 GHz, 41 GHz, 42 GHz, 42.2 GHz, 43 GHz, 44 GHz, 45 GHz, 46 GHz, 47 GHz, 48 GHz, 49 GHz, 50 GHz, 51 GHz, 52 GHz, 53 GHz, 54 GHz, or 55 GHz. In an embodiment, the oscillation frequency is 42194±10 MHz and linearly modulated within 100 MHz band around this frequency. In an embodiment, the oscillation frequency is 53534±10 MHz and linearly modulated within a 50 MHz band around this frequency. The electromagnetic waves may be delivered with any electronic or photonic device known within the art, such as a YAV-1 therapeutic device, based on an IMPATT diode oscillator. The electromagnetic waves may have a power density below 1 mW/cm$^2$, such as between 0.004 mW/cm$^2$ and 0.2 mW/cm$^2$, e.g. about 0.1 mW/cm$^2$.

The effect of the EHF treatment is shown in FIG. 1.

FIG. 1A is a growth curve of untreated cells. $N/N_0$ (Y axis) is the ratio of the number of cells N in the culture to the starting number $N_O$ and t (in hours, X axis) is the culture-development time. FIG. 1B is a growth curve of treated cells. The frequencies of the oscillations generated by the cells can be synchronized by corresponding reorganization of the information structures of the cells, which causes differences in the division-cycle durations of individual cells to be practically eliminated with the result of "steps" on the growth curve. It is apparent from FIG. 1B that after each division cycle the number of cells is doubled synchronously, so that the dependence of the number of cells on time is represented by a step curve.

Table 1 is an overview of the minimum time ($t_0$, min) needed to synchronize cell division of all cells at different power density levels (P, mW/cm$^2$) with a radiation frequency 42.2 GHz.

TABLE 1

| $t_0$, min | P, mW/cm$^2$ |
|---|---|
| 126 | 0.005 |
| 103 | 0.009 |
| 81 | 0.015 |
| 60 | 0.026 |
| 49 | 0.040 |
| 38 | 0.077 |
| 36 | 0.130 |
| 34 | 0.209 |

Table 2 is an overview of time required ($t_0$, min) to synchronize cell division of 15 percent of the cells at different power density levels (P, mW/cm$^2$) with a radiation frequency of 42.2 GHz.

TABLE 2

| $t_0$, min | P, mW/cm$^2$ |
|---|---|
| 111 | 0.003 |
| 86 | 0.006 |
| 65 | 0.012 |
| 45 | 0.024 |
| 38 | 0.037 |
| 33 | 0.052 |
| 31 | 0.074 |
| 27 | 0.130 |
| 26 | 0.200 |

Thus, in an embodiment, EHF treatment time is between 20 and 120 minutes.

In an embodiment, the method further comprises the step of growing the treated yeast cells in the growth medium. The growth may be aborted at any time, when a desired cell concentration is achieved.

According to a specific embodiment, the growth medium is wort, i.e. a tonic malt beverage is obtained from wort and yeast. Any kind of yeast may be used. Any kind of wort may be used. However, in one embodiment, the wort is obtained from a brewery. In another embodiment, the wort is made from barley malt. In yet another embodiment, the wort is made from wort concentrates.

If the wort is obtained from a brewery or if wort concentrates are used, the weight fraction of dry matters may be adjusted, i.e. with the following formula:

$$W = Q * (C_o/C_d - 1)$$

Where W is the volume in liters (L) of water to be added for dilution of the original wort, Q is the volume (L) of the original (starting) wort, obtained i.e. from a brewery or in concentrated form; $C_o$ is extract content of original wort in wt %; and $C_d$ is the weight fraction of dry matters in the diluted wort.

In an embodiment, the weight fraction of dry matters in the diluted wort may be around 11 wt % (11 wt % wort), such as from 10.5 wt % to 11.4 wt %.

If the wort is made from barley malt, the amount of raw materials needed for producing 100 L wort may be calculated i.e. with the formula:

$$C = \frac{wf * \rho * cc * 100 * 100}{(E_{avg} - L_B) * (100 - B)}$$

Where C is specific malt consumption, in kg/100 L water; wf is weight fraction of dry matters in the original wort in wt %; p is density ratio of wort, in g/100 g; cc is the coefficient of compression between volume of wort and volume of final beverage; $E_{avg}$ is the content of malt used, in wt %; $L_B$ represents content losses, in %; and B represents volume losses, in %.

In one embodiment, the wort produced according to any of the abovementioned embodiments is sterilized in an autoclave chamber with a pressure of 0.05 MPa during 20 minutes. The wort may then be stored in sealed containers up to 6 months at temperatures between 18 and 20° C.

According to another embodiment, the wort produced according to any of the abovementioned embodiments may also be pasteurized such as by heating it to between 70 and 75° C. for more than 30 minutes. The wort may then be stored in sealed containers up to 2 weeks at temperatures between 18 and 20° C.

According to one embodiment, S. cerevisiae is revived by suspension in a small volume of sterilized 11 wt % wort. It is important that no other microorganisms contaminate the wort.

The revived culture is subsequently inoculated on a number of Petri dishes with agarized wort, to obtain pure yeast culture. This may be confirmed by microscope.

Prior to EHF-treatment, yeast from one of the dishes with pure culture sterile are transferred into the tube containing sterile 11 wt % wort, such as between 10 to 12 mL. The cultures are grown until skim appears, typically at 25 to 28° C. during 20 to 24 hours.

The yeast culture is then treated in an EHF-field. This may be done by first filling sterile Petri dishes with yeast suspension. The dish is then covered and placed in an EHF-unit. Such a unit may be any unit generating electromagnetic oscillations in the EHF-range. EHF-treating time is preferably less than 60 minutes. The power density of EHF-oscillations is preferably about 0.1 mW/cm$^2$. The oscillation frequency is within the range of 30 to 300 GHz. The electromagnetic waves may be within the range from about 35 to about 65 GHz, such as 40 GHz, 41 GHz, 42 GHz, 42.2 GHz, 43 GHz, 44 GHz, 45 GHz, 46 GHz, 47 GHz, 48 GHz, 49 GHz, 50 GHz, 51 GHz, 52 GHz, 53 GHz, 54 GHz, or 55 GHz. In an embodiment, the oscillation frequency is 42194±10 MHz and linearly modulated within a 100 MHz band around this frequency. In an embodiment, the oscillation frequency is 53534±10 MHz and linearly modulated within a 50 MHz band around this frequency. The electromagnetic waves may be delivered with any electronic or photonic device known within the art, such as a YAV-1 therapeutic device, based on an IMPATT diode oscillator.

In an embodiment, the frequency modulation of the electromagnetic waves is from 0% to about 0.5% of the respective average frequency, such as 0.5% of the respective average frequency.

After treatment in the EHF-unit, the abovementioned treated suspension is transferred to a tube, such as a 50 to 100 mL tube, containing sterile 11 wt % wort. The cells are allowed to grow until skim appears, typically during 20 to 24 hours at 25 to 28° C. This is the seed material.

The seed material is then added to pasteurized or sterilized wort, typically 2 to 3 L, filled in containers (tube, can, etc.) of nominal capacity slightly larger than the amount word, typically 4 to 5 L, and cultivated until a cell concentration of 30 million cells/mL is achieved, typically after 20 to 24 hours at 25 to 28° C.

In another embodiment, if large volumes of beverage are produced, the above-mentioned treatment may be implemented in several stages by adding the result of a previous cultivation cycle as seeding material to sterile wort with a ration of 1:10 seeding material:wort. The cells are allowed to grow until skim appears, typically during 20 to 24 hours at 25 to 28° C. The last stage of the beverage production stage is deemed to be finished when a cell concentration no less than 30 million cells/mL is achieved.

Upon completion of the production stage beverage is ready for selling and may be transferred to suitable transport vessels, e.g. bottles or cans. If storage is required, beverage may be cooled to about 2 to 4° C. and may then be stored, such as up to three days.

The invention can be implemented in any suitable form including food products, feed, other drink products, etc., or any combination of these, without departing from the gist of the invention.

The elements and components of an embodiment of the invention may be physically, functionally and logically implemented in any suitable way. Indeed, the functionality may be implemented in a single composition, in a plurality of compositions or as part of other functional compositions.

In an embodiment, the composition may be used in a method for the treatment or prevention of neurodegenerative diseases or disorders in a subject, such as a human.

Treated Yeast Cells

The following is an enabling embodiment of a production procedure. However, many different alternate production procedures are possible within the scope of the invention, which will be recognized by a person skilled in the art.

Wort was obtained from a brewery and the weight fraction of dry matters in the diluted wort was adjusted to 11 wt % (11 wt % wort).

The wort was sterilized in an autoclave chamber with a pressure of 0.05 MPa during 20 minutes and stored between 18 and 20° C.

Yeast, S. cerevisiae was revived by suspension in a small volume of sterilized 11 wt % wort under sterile conditions.

The yeast was inoculated on a number of Petri dishes with agarized wort, to obtain pure yeast culture. This was confirmed by microscope.

Prior to EHF-treatment, yeast from one of the dishes with pure culture sterile was transferred into the tube containing 11 mL of sterile 11 wt % wort. The cultures were grown at 28° C. during 20 to 24 hours until skim appears.

The yeast culture was then treated in an EHF-field. This was done by first filling sterile Petri dishes with yeast suspension. The dish was then covered and placed in an EHF-unit, generating electromagnetic oscillations in the EHF-range. EHF-treating time was 40 minutes. The power density of EHF-oscillations was kept near 0.1 mW/cm$^2$. The oscillation frequency was 53534±10 MHz and was linearly modulated within a 50 MHz band around this frequency. The electromagnetic radiation was generated by the YAV-1 therapeutic device, based on an IMPATT diode oscillator.

After treatment in the EHF-unit, the abovementioned treated suspension was transferred to a tube of 75 mL containing sterile 11 wt % wort. The cells were allowed to grow during 22 hours at 28° C. until skim appears. This was the seed material.

The seed material was then added to 3 L pasteurized or sterilized wort filled in tubes of nominal capacity of 5 L and cultivated until a cell concentration of 30 million cells/mL was achieved. These treated yeast cells were given to the mice according to below.

Experimental

Mice treated with 1-methyl-4-phenyl-1,2,3,6-tetrahydropyridine (MPTP) to induce symptoms similar to neurodegenerative diseases or disorders were given a composition comprising treated yeast cells according to above, in conjunction with exercise.

It is well known within the art that MPTP leads to similar symptoms to that of patients suffering from neurodegenerative diseases or disorders, such as bradykinesia, resting tremor and rigidity. MPTP in itself does not appear to be toxic but it is known to cross the blood-brain barrier after which a biotransformation into a toxic metabolite involving monoamine oxidase (MAO) occurs. MAO is the first step in the conversion of MPTP to the 2,3-dihydropyridinium intermediate (MPDP+). MPDP+ oxidizes on impulse, shaping the 1-methyl-4-phenylpyridinium ion (MPP+). MPP+ is the most important toxic metabolite of MPTP, which gives the symptomatic effect. In the model, age plays a vital role when injecting MPTP in mice, since many neurodegenerative diseases or disorders are known to have a late onset in humans.

Materials and Methods

Initial Experiments

Altogether 90 two-months-old male C57 BL/6 mice originating from Scanbur B & K, Sollentuna, Sweden, weighing 27±2 g were used in the experiment. Following the arrival at the laboratory, the mice were allowed to acclimatize for one week in a room with controlled temperature (22±1° C.), humidity (55±5%) and they all had access to food, R35 pellets from Lantmännen, Sweden and tap water ad libitum. There was a constant light-dark cycle (12 hr on/12 hr off; lights on between 6.00 AM and 6.00 PM) in the room. The mice were divided into six groups, 15 animals each, and housed in wire topped laboratory polycarbonate cages (55*35*18 cm). The cages were marked with numbers in order to separate them. In each cage there were two nests in which the mice were able to hide and sleep.

Altogether 16 running wheels measuring 17.5 cm in diameter, Deluxe from Living World, were used. To prevent the mice from evading the wheels, the wheels were enclosed with plastic walls. A piece of plastic coating was cut out and formed in the same diameter as the wheel and placed on each side of the wheel, on one side attached with Velcro to allow the mouse to enter and come out from the wheel. On the other side of the wheel the plastic was glued on to the exercise wheel.

A motor-activity test apparatus comprising macrolon rodent test cages (40*25*15 cm) was used. Each test chamber, i.e. motor activity test cage, was placed in a sound-proof wooden box with 12 cm thick walls and front panels and a small double-glass window to allow observation. Each box had a dimmed lighting, all placed within two series of infrared beams (at two different heights, one low and one high, 2 and 8 cm, respectively, above the surface of the sawdust, 1 cm deep), was used to measure spontaneous and/or drug-induced motor activity of MPTP and control mice (Rat-O-Matic, ADEA Electronic AB, Uppsala, Sweden). The distance between the infra-red beams was as follows: the low-level beams were 73 mm apart lengthwise and 58 mm apart breadthwise in relation to the test chamber; the high-level beams were placed only next to each long side of the test chamber were 28 mm apart.

FIG. 2 A is a side view image of the motor-activity test apparatus and FIG. 2 B is a front view of the same apparatus. In a base support 20 cages and sensors are positioned. The cage is a transparent plastic cage 21 with a perforated aluminum lid 22 on top. The plastic cage 21 is resting on an elastic rubber support 23. A pick-up 24 is mounted on a lever with a counterweight and a number of infrared (IR) detectors 25 are positioned in proximity to the plastic cage 21.

During all the tests, saline was distributed as vehicle. When applicable, 1-Methyl-4-Phenyl-1,2,3,6-tetrahydropyridine (MPTP) (Research Biochemical Inc., Natick, Mass. USA), was dissolved in vehicle before distribution.

Similarly, L-dopa (Hässle, Mölndal, Sweden) was dissolved in saline before distribution. L-dopa is known within the art to treat neurodegenerative diseases or disorders. The neurotransmitter system takes account of three neurotransmitters, noradrenaline (NE), dopamine (DA) and serotonin (5HT). The amino acid precursor to DA, tyrosine (TYR) is transported into the nervous system from the blood stream by an active transport pump. TYR acts inside the neuron on three enzymes in succession. First TYR acts with hydroxylase which regulate the NE synthesis. Tyrosine hydroxylase (TOH) next converts TYR into dihydroxyphenyl-alanine (DOPA). The second enzyme, DOPA decarboxylas (DDC), then acts and converts DOPA into DA. The third enzyme dopamine beta hydroxylase converts DA into NE. At least five pharmacological subtypes of DA-receptors are known. In PD the dopamine 2 (D2)-receptor is stimulated by dopaminergic agonists such as L-dihydroxyphenyl-alanine (L-dopa). L-dopa, the precursor to DA, is an amino acid metabolized into DA both peripherally and centrally. L-dopa can as opposed to DA cross the blood-brain-barrier, since L-dopa uptake by L-amino acid carrier crosses the blood-brain-barrier. The administration of L-dopa is combined with decarboxylas inhibitors to decrease the peripheral metabolism. After some years of treatment the effect of L-dopa decline and the patients develop dyskinesia, and/or on-off symptoms. Anyhow, L-dopa is the most commonly used treatment within the art, and is therefore used here as a reference.

The total of 90 2-months-old C57 BL/6 male mice were divided into 6 groups according to table 3.

TABLE 3

Overview of test subdivision.

| Group | 1 week | Treatment | 6 weeks |
|---|---|---|---|
| 1 | | Vehicle | |
| 2 | wheel | Vehicle | wheel |
| 3 | | MPTP | |
| 4 | wheel | MPTP | wheel |
| 5 | | MPTP | yeast |
| 6 | wheel | MPTP | yeast + wheel |

After the first week of acclimatizing the mice in group 1 and 2 were given 2*2 ml/kg vehicle and the mice in group 3, 4, 5 and 6 were given 2*40 mg/kg MPTP, S.C., at a 16-hr interval, to induce symptoms of a neurodegenerative disease or disorder. The exercising mice were allowed to rest for 3 days after the treatment before the wheel-running 30 min/day, 5 days/week for 6 weeks started. The exercise was performed in a behavioral test room. The mice were placed into the running wheels by grabbing them by their tail and thereafter the plastic was fastened. At the end of each exercise session the plastic was removed and the mouse was allowed to come out of the wheel and walk into its home cage by themselves. Group 5 and 6 were offered treated yeast, 0.5 ml/subject containing one million activated yeast cells, orally twice a week (Mondays and Thursdays) during 6 weeks simultaneously with the exercise. Group 3 and 4 were handled in the same way as group 5 and 6 even though they were not given any oral treatment.

After the period of wheel-running the mice were tested for motor activity in a specially arranged test room. This test room, in which 12 ADEA activity test chambers were placed, was well-secluded and used only for this purpose. The mice were tested one by one for one hour, and the mouse was placed in the middle of the chamber. The following parameters were recorded:

The variable LOCOMOTION was measured by the low grid of infra-red beams. Counts were registered only when the mouse in the horizontal plane ambulated around the test-cage.

The variable REARING was registered throughout the time when at least one high-level beam was interrupted, i.e., the number of counts was proportional to the amount of time spent rearing.

The variable TOTAL ACTIVITY was measured by a sensor (a pick-up similar to a gramophone needle, mounted on a lever with a counterweight) with which the test cage was constantly in contact.

The sensor registered all types of vibration received from the test cage, such as those produced both by locomotion and rearing as well as shaking, tremors, scratching and grooming.

All three behavioral parameters were measured over three successive 20-min. periods. Motor-activity parameters were tested on one occurrence only, over three successive 20-min periods. After the spontaneous activity the mice were tested for induced activity, which are movements influenced by exercise and Treated yeast. The mice were injected subcutaneously (s.c.) with a sub threshold dose of L-dopa, 0.5 mg/kg. Then the mice were placed one by one into the test chambers again for 4 h. Only the last 3 h measurement was taken in count to exclude the motion resulted from handling and the injection procedure. After the tests were performed the mice were cervically dislocated and the striatal regions were rapidly dissected out and stored at −80° C. until the neurochemical analysis took place.

The neurochemical analysis was performed by using a high performance liquid chromatograph with electrochemical detection (HPLC-EC) to assay DA and the internal standard Carbidopa. The frozen striatum was weighed and homogenized in 1 ml 0.1 M perchloric acid. Carbidopa was added as an internal standard. After centrifugation (10 000 rpm, i.e. 12519*g, 4° C., 15 min) and filtration, a volume of 0.05 ml of the homogenate was diluted 1:4 with mobile phase and 20 µA was injected into the HPLC-EC. The HPLC system consisted of a Bischoff pump model 2250 (Bischoff, Germany), an autosampler/autoinjector fitted with a tray cooling kept at 5° C. (Midas, Spark Holland), an analytical column (Reprosil-Pur, C18-AQ, 250*4 mm, 5 µm fitted with a guard column (A. Maisch, Deutschland) kept at 30° C., and a Coulochem It ESA multi-electrode detector fitted with a Model 5011-A dual analytical cell (ESA Analytical, Chelmsford, Mass., USA) operating at an oxidation potential of +300 mV. The mobile phase, pH 3.0±0.1, consisted of 100 mM $NaH_2PO_4$, 0.5 mM 1-octanesulfonic acid, 1 mM EDTA and methanol 10%. The flow rate was 0.7 ml/min.

The spontaneous locomotion, rearing and total-activity data over 3 consecutive 20-min periods in the activity test chambers were submitted to a split-plot ANOVA design, well known within the art. The results from the dopamine levels in striatum and the restorative effect of 5 mg/kg L-dopa on locomotion, rearing and total activity, the sum of the last 3 of 4 hours (the effect of the s.c.-injection excluded the first hour) were submitted to a one-way ANOVA design. Post-hoc pairwise testing between the different treatment groups was performed with Tukey's HSD test, well known within the art. Throughout, the 1% level of significance was maintained, unless otherwise stated.

Further Experiments

Recovery Study 1

Three weeks following arrival, two groups (n=10) of mice according to above were administered MPTP (40 mg/kg, s.c.) and two groups administered saline (Vehicle, 2 ml/kg) on the Friday of the 4th week following arrival. Similar administrations of MPTP or Vehicle were maintained on each Friday on the 5th, 6th and 7th weeks following arrival. In each case, behavioural testing in the activity test chambers was carried out prior to MPTP/Vehicle administration (Tests 1-5). Concurrently, during the 4th-7th weeks and the 8th week one Vehicle and one MPTP group were given 30-min exercise sessions over four days each week (mon-thurs.). Following this, exercise sessions were terminated but all the mice were tested during the 10th and 12th weeks (Tests 6 & 7: fri.). was designed to examine whether or not a single weekly dose of MPTP (40 mg/kg), instead of the standard 2×40 mg/kg dosage separated by 24 hours, would provide a progressive hypokinesic increment when activity testing occurred one week after MPTP administration. The experiment was designed also to test whether or not a consecutive four-day regime of wheel-running exercise would attenuate the hypokinesic effects of the neurotoxin. Table 4 presents the experimental design and treatment of mice administered either MPTP or Vehicle, with or without five weeks of running wheel exercise.

TABLE 4

Experimental design and treatment of mice administered either MPTP or Vehicle, with or without six weeks of running wheel exercise.

|  |  | Vehicle | MPTP | Veh + Exer | MPTP + Exer |
|---|---|---|---|---|---|
| 1st-3rd week |  | Acclimatization and exposure to running-wheels | | | |
|  | Monday | cage | Cage | Exer | Exer |
|  | Tuesday | cage | Cage | Exer | Exer |
| 4th week | Wednesday | cage | Cage | Exer | Exer |
|  | Thursday | cage | Cage | Exer | Exer |
| Test 1■ | Friday | Test + sal | Test + MPTP* | Test + sal | Test + MPTP* |
|  | Monday | cage | Cage | Exer | Exer |
|  | Tuesday | cage | Cage | Exer | Exer |

TABLE 4-continued

Experimental design and treatment of mice administered either MPTP or Vehicle, with or without six weeks of running wheel exercise.

|  |  | Vehicle | MPTP | Veh + Exer | MPTP + Exer |
|---|---|---|---|---|---|
| 5th week | Wednesday | cage | Cage | Exer | Exer |
|  | Thursday | Cage | Cage | Exer | Exer |
| Test 2■ | Friday | Test + sal | Test + MPTP* | Test + sal | Test + MPTP* |
|  | Monday | Cage | Cage | Exer | Exer |
|  | Tuesday | cage | Cage | Exer | Exer |
| 6th week | Wednesday | Cage | Cage | Exer | Exer |
|  | Thursday | cage | Cage | Exer | Exer |
| Test 3■ | Friday | Test + sal | Test + MPTP* | Test + sal | Test + MPTP* |
|  | Monday | Cage | Cage | Exer | Exer |
|  | Tuesday | cage | Cage | Exer | Exer |
| 7th week | Wednesday | Cage | Cage | Exer | Exer |
|  | Thursday | cage | Cage | Exer | Exer |
| Test 4■ | Friday | Test + sal | Test + MPTP* | Test + sal | Test + MPTP* |
|  | Monday | Cage | Cage | Cage | Cage |
|  | Tuesday | cage | Cage | cage | Cage |
| 8th week | Wednesday | Cage | Cage | Cage | Cage |
|  | Thursday | cage | Cage | cage | Cage |
| Test 5■ | Friday | Test | Test | Test | Test |
| 10th week | Tues.-Thurs. | 30-min SMA■ test (Test 6) + 120 min L-Dopa test | | | |
| 12th week | Tues.-Thurs. | 30-min SMA■ test (Test 7) + 120 min L-Dopa test | | | |
| 14th week |  | Sacrifice + dessication of striatum | | | |

*MPTP (40 mg/kg)
■ Spontaneous motor activity over 60 min

Recovery Study 2

In a second recovery study, mice were administered single weekly doses of MPTP (1×40 mg/kg, s.c.), after a test of spontaneous motor activity, that followed 4 consecutive days of wheel-running activity (see Table 5, below), over four consecutive weeks, with a similar procedure during the 5$^{th}$ week except that there was no administration of MPTP after the test of motor activity. After this, all the mice were left for two weeks without treatment or wheel-running exercise and then tested again on the spontaneous motor test followed by the L-Dopa-induced motor activity test. After another two weeks without treatment or wheel-running exercise, all the mice were given a final test of spontaneous motor test followed by the L-Dopa-induced motor activity test (see Table 5, below). On the following week, MPTP and Vehicle mice were sacrificed and striatal regions dissected out for neurochemical analysis.

After this, all the mice were left for two weeks without treatment or wheel-running exercise and then tested again on the spontaneous motor test followed by the L-Dopa-induced motor activity test. After this, all the mice were then maintained under conditions of wheel-running exercise or sedentary placement in plexiglass cages over the following nine weeks but tested at two-week intervals where both spontaneous motor activity (Tests 1-14) and L-Dopa-induced activity (Tests 1-5, during weeks 6, 8, 10, 12 and 14 of the experiment) were assessed. On the following week (week 15), MPTP and Vehicle mice were sacrificed and frontal cortex, parietal cortex, hippocampus and striatal regions dissected out for neurochemical analysis of DA and BDNF. According to this design, only one vehicle group (non-exercised were included) show that wheel-running exercise produced no behavioural alterations in the vehicle-injected animals.

TABLE 5

The experimental design and treatment of mice administered either MPTP or Vehicle, with or without three weeks of running wheel exercise was carried out.

| Time & Test | Day | Vehicle | MPTP | MPTP + Exercise |
|---|---|---|---|---|
| Week 1-4 | Monday | Cage | Cage | Exer |
|  | Tuesday | Cage | Cage | Exer |
|  | Wednesday | Cage | Cage | Exer |
|  | Thursday | Cage | Cage | Exer |
| Test 1-4* | Friday | Test + sal | Test + MPTP■ | Test + MPTP■ |
| Week 5-8 | Monday | Cage | Cage | Exer |
|  | Tuesday | Cage | Cage | Exer |
|  | Wednesday | Cage | Cage | Exer |
|  | Thursday | Cage | Cage | Exer |
| Test 5-8* | Friday | Test + sal | Test | Test |
| Week 9-14 | Monday | Cage | Cage | Exer |
|  | Tuesday | Cage | Cage | Exer |
|  | Wednesday | Cage | Cage | Exer |
|  | Thursday | Cage | Cage | Exer |
| Test 9-14* | Friday | Test + sal | Test | Test |

Spontaneous motor activity tests over 60 min intervals and subthreshold L-Dopa tests are indicated.
■ MPTP (40 mg/kg) injected during the 1st four weeks
*Spontaneous Motor Activity over 60 min
**L-Dopa (5 mg/kg, s.c.) after 60-min habituation to test cages Restoration Study A restoration study was performed, wherein mice were administered single weekly doses of MPTP (1×30 mg/kg, s.c.), after a test of spontaneous motor activity, without wheel-running activity, over the 1st two consecutive weeks, but with wheel-running exercise initiated on the 3rd week for the MPTP+Exer(2) group; the MPTP+Exer(4) group continued without wheel-running exercise during the 3rd and 4th weeks, but received wheel-running from the 5th week onwards. The procedure of wheel-running for the MPTP+Exer(2) and MPTP+Exer(4) groups during the 5th to the 10th weeks was then maintained except that there was no further administration of MPTP after the test of motor activity. Throughout the 30-min periods when the MPTP+Exer(2) and MPTP+Exer(4) groups were allowed wheel-running exercise, the mice in the Vehicle and MPTP groups were in single cages placed in the same room for 30-min periods. After this, all the mice were left for two weeks without treatment or wheel-running exercise and then tested again on the spontaneous motor test followed by the L-Dopa-induced motor activity test. After this, all the mice were then maintained under conditions of wheel-running exercise or sedentary placement in plexiglass cages over the following nine weeks but tested at two-week intervals where both spontaneous motor activity (Tests 1-14) and L-Dopa-induced activity (Tests 1-5, during weeks 6, 8, 10, 12 and 14 of the experiment) were assessed. On the following week (week 15), MPTP and Vehicle mice were sacrificed and frontal cortex, parietal cortex, hippocampus and striatal regions dissected out for neurochemical analysis of DA and BDNF. According to this design, only one vehicle group (non-exercised was included) show that wheel-running exercise produced no behavioural alterations in the vehicle-injected animals. Table 6 is an overview of the experimental design and treatment of mice administered either MPTP or Vehicle, with or without three weeks of running wheel exercise as carried out in Experiment II. Spontaneous motor activity tests over 60-min intervals and subthreshold L-Dopa tests are indicated.

TABLE 6

The experimental design and treatment of mice administered either MPTP or Vehicle, with or without three weeks of running wheel exercise was carried. Spontaneous motor activity tests over 60 min intervals and subthreshold L-Dopa tests are indicated.

|  | Vehicle | Mptp | Mptp + Exer (3 ◇) | M + Exer (3 ◇) + Y | M + Exer (5 ◇) | M + Exer (5 ◇) + Y |
|---|---|---|---|---|---|---|
| Monday | cage | Cage | Cage | Cage | Cage | Cage |
|  | cage | Cage | Cage | Cage | Cage | Cage |
| Week 1 | cage | Cage | Cage | Cage | Cage | Cage |
|  | cage | Cage | Cage | Cage | Cage | Cage |
| Friday: T1■ | Test + sal | Test + Mptp | Test + Mptp | Test + Mptp | Test + Mptp | Test + Mptp |
| Monday | cage | Cage | Cage | Cage | Cage | Cage |
|  | cage | Cage | Cage | Cage | Cage | Cage |
| Week 2 | cage | Cage | Cage | Cage | Cage | Cage |
|  | Cage | Cage | Cage | Cage | Cage | Cage |
| Friday: T2■ | Test + sal | Test + Mptp | Test + Mptp | Test + Mptp | Test + Mptp | Test + Mptp |
| Monday | Cage | Cage | Exer | Exer + Y | Cage | Cage |
|  | cage | Cage | Exer | Exer + Y | Cage | Cage |
| Week 3 | Cage | Cage | Exer | Exer + Y | Cage | Cage |
|  | cage | Cage | Exer | Exer + Y | Cage | Cage |
| Friday: T3■ | Test + sal | Test + Mptp | Test + Mptp | Test + Mptp | Test + Mptp | Test + Mptp |
| Monday | Cage | Cage | Exer | Exer + Y | Cage | Cage |
|  | cage | Cage | Exer | Exer + Y | Cage | Cage |
| Week 4 | Cage | Cage | Exer | Exer + Y | Cage | Cage |
|  | cage | Cage | Exer | Exer + Y | Cage | Cage |
| Friday: T4■ | Test + sal | Test + Mptp | Test + Mptp | Test + Mptp | Test + Mptp | Test + Mptp |
| Monday | Cage | Cage | Exer | Exer + Y | Exer | Exer + Y |
|  | cage | Cage | Exer | Exer + Y | Exer | Exer + Y |
| Week 5&6 | Cage | Cage | Exer | Exer + Y | Exer | Exer + Y |
|  | cage | Cage | Exer | Exer + Y | Exer | Exer + Y |
| Fri. v5: | cage | Cage | Exer | Exer + Y | Exer | Exer + Y |
| Fri. v6: T5* | Test | Test | Test | Test | Test | Test |
| Monday | Cage | Cage | Exer | Exer + Y | Exer | Exer + Y |
|  | cage | Cage | Exer | Exer + Y | Exer | Exer + Y |
| W. 7&8 | Cage | Cage | Exer | Exer + Y | Exer | Exer + Y |
|  | cage | Cage | Exer | Exer + Y | Exer | Exer + Y |
| Fri. w7: | cage | Cage | Exer | Exer + Y | Exer | Exer + Y |
| Fri. w8: T6* | Test | Test | Test | Test | Test | Test |
| Monday | Cage | Cage | Exer | Exer + Y | Exer | Exer + Y |
|  | cage | Cage | Exer | Exer + Y | Exer | Exer + Y |
|  | Cage | Cage | Exer | Exer + Y | Exer | Exer + Y |

TABLE 6-continued

The experimental design and treatment of mice administered either MPTP or Vehicle, with or without three weeks of running wheel exercise was carried. Spontaneous motor activity tests over 60 min intervals and subthreshold L-Dopa tests are indicated.

|  | Vehicle | Mptp | Mptp + Exer (3 ◇) | M + Exer (3 ◇) + Y | M + Exer (5 ◇) | M + Exer (5 ◇) + Y |
|---|---|---|---|---|---|---|
|  | cage | Cage | Exer | Exer + Y | Exer | Exer + Y |
|  | cage | Cage | Exer | Exer + Y | Exer | Exer + Y |
| Fri. w: T7* | Test | Test | Test | Test | Test | Test |
| Week 10: Fri T8* | Treated yeast, no Exercise |||||| 
| Week 11 | Neurochemistry test ||||||

■ SMA only;
*SMA + L-Dopa
3 ◇ = Exer + Treated yeast starts w. 3;  ◇ 5 = Exer + Treated yeast starts w. 5

Results and Discussion

Initial Experiments

Administration of MPTP, to 6-week-old mice resulted in the following alteration of the DA content in striatum depending on the post treatment, revealed by HPLC analysis 7 weeks after MPTP treatment. Administration of MPTP triggered decreased DA content in striatum, compared to the vehicle group. Thus, one-way ANOVA indicated significant BetweenGroups effects for DA content in striatum F(5, 30)=35.92, P<0.0001. FIG. 3 illustrates the DA content in striatum. The y axis represents the level of dopamine in ng/mg net weight. Along the x axis, the different samples are shown as columns. Column 31 is vehicle only (control sample), group 1. Column 32 is vehicle in combination with exercise, group 2. Column 33 is MPTP 40 mg/kg, group 3. Column 34 is MPTP 40 mg/kg in combination with exercise, group 4. Column 35 is MPTP 40 mg/kg in combination with treated yeast, group 5. Column 36 is MPTP 40 mg/kg in combination with treated yeast and exercise, group 6.

The columns show that treated yeast has an effect on the level of dopamine in striatum, since group 5 mice has higher levels than group 3 mice. Treated yeast in combination with exercise gives an even higher effect, as shown by column 6.

Pairwise testing using Tukey's HSD test revealed the following differences: MPTP decreased DA content in all treated groups compared to vehicle. Exercise partly antagonized the decrease but no additional effect was seen from treated yeast. Administration of vehicle or MPTP followed by exercise over 30-min consecutive 5-day periods each week and/or treated yeast supplementation two times a week for 6 weeks partly restored the hypoactivity due to MPTP. By itself treated yeast did not affect the hypokinesic effect of MPTP. Thus, split-plot ANOVA indicated significant Treatment*Time interactions: Locomotion: F(IO, 108)=57.21, P<0.0001; Rearing: F(IO, 108)=89.56, P<0.0001; and Total activity: F(10, 108)=89.56, P<0.0001. FIG. 4 presents means and SD values for locomotion, rearing and total activity.

Pairwise testing using Tukey's HSD test revealed differences between the different MPTP post treatments and the vehicle group. In vehicle mice there was a distinct decrease in activity in all spontaneous behaviors over the 60 min period. Such a decrease is a normal profile of spontaneous behaviour. Vehicle plus exercise did not differ from the vehicle unaccompanied. The hypoactivity produced by MPTP treatment compared to the vehicle treatment characterized by the reduced locomotion, rearing and total-activity mean counts was not affected by treated yeast alone. In contrast, exercise alone partly restored the locomotion during the 1st and 2nd period. Also the combination, exercise plus treated yeast, partly restored locomotion the 1st and 2nd period together with a restorative effect on rearing. For locomotion during the 1st period and rearing 2nd period treated yeast plus exercise significantly reduced the hypoactivity as opposed to exercise alone.

Induced behavior was studied after exposure to a sub threshold dose of 5 mg/kg L-dopa. This dose of L-dopa covers by itself no effects on hypoactive mice pretreated with 40 mg/kg MPTP. The sum of the locomotion, rearing and total-activity counts of the last 3 of 4 hrs (activity produced by handling and injection during the first hr excluded) measurement of induced behavior was submitted to a one-way ANOVA. Significant Between-Groups effects were discovered:

Locomotion $F(5, 54)=44.19$ $P<0.0001$; Rearing $F(5, 54)=33.50$ $P<0.0001$ and Total activity $F(5, 54)=25.69$ $P<0.0001$.

Figure 4A:
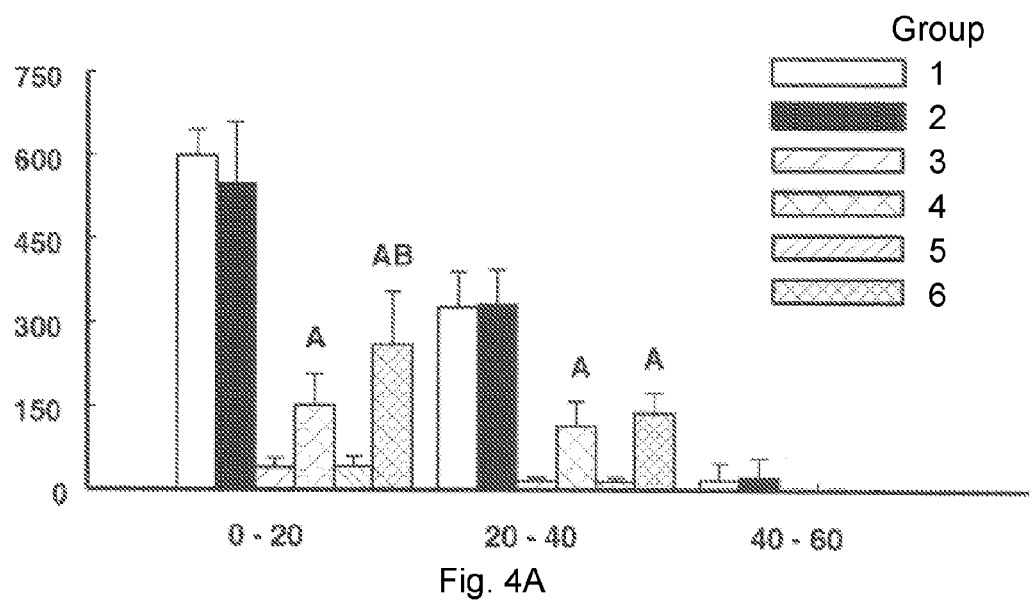
FIG. 4 are diagrams showing mean and SD values for locomotion, rearing and total activity, at different times respectively.
Figure 4B:
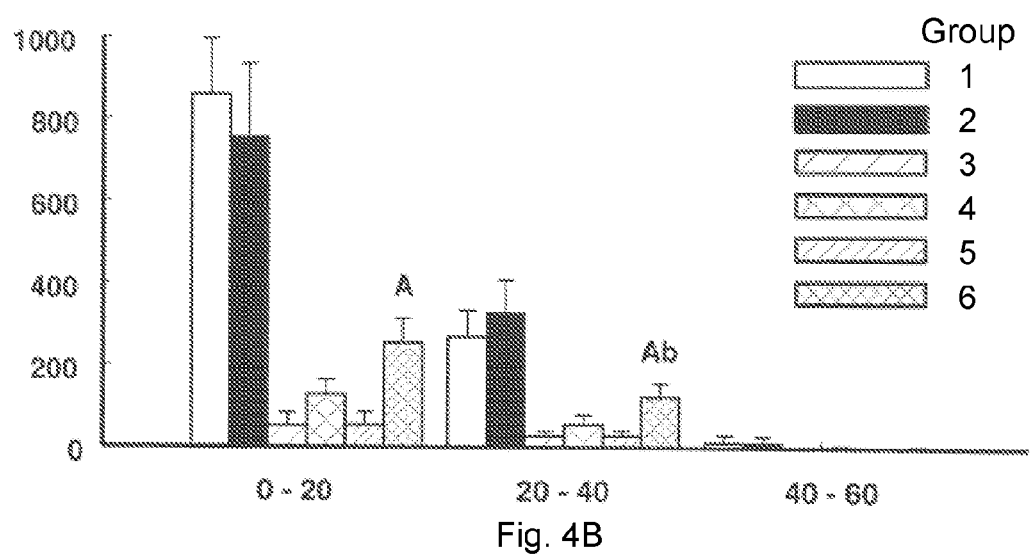
Figure 4C:
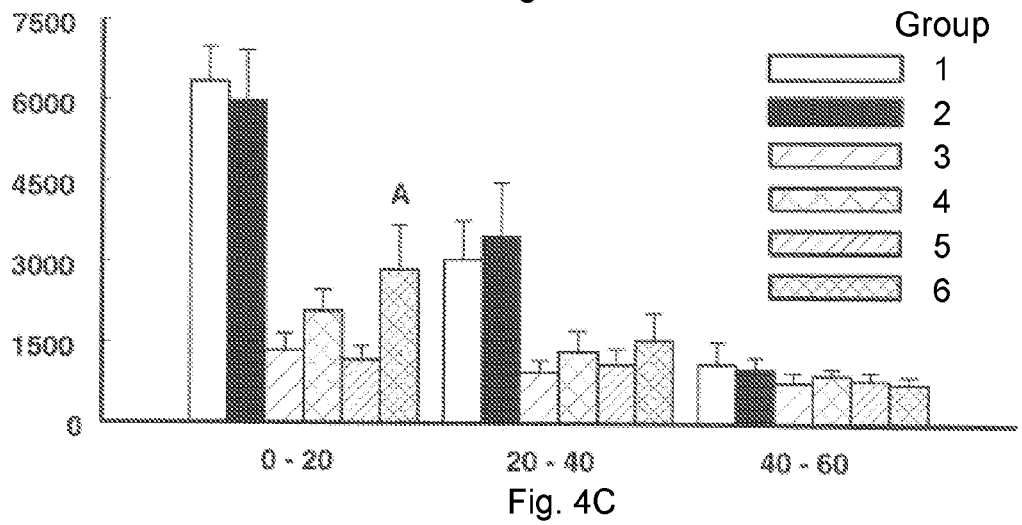

FIG. 4 summarizes the results. Means and SD values for locomotion (FIG. 4A), rearing (FIG. 4B) and total activity (FIG. 4C) for the 3 hrs after L-dopa administration are shown. Treated yeast produced a significant addition of locomotion and rearing in combination with exercise. Letters (uppercase 0.01 and lower case 0.05) indicate significant differences, where A represents comparison between exercise and non-exercise and B, between groups given treated yeast treated. Pairwise testing using Tukey's HSD test revealed the following differences: L-dopa did not show any beneficial effects on MPTP treated mice without exercise or only post-treatment with treated yeast. Exercise and exercise+treated yeast groups were significantly less hypoactive for all three variables compared to no exercise and treated yeast alone. Treated yeast produced a significant addition of locomotion and rearing in combination with exercise.

The present study examined the predisposition for physical exercise in the form of daily wheel-running by itself or in combination with treated yeast, to restore, notwithstanding partially, hypokinesia, and neurochemical deficits in general and DA depletion in particular, induced by MPTP administration (2*40 mg/kg). The results are summarized as follows:

1. The hypokinesia due to MPTP administration was restored partially by daily exercise, which effect was increased through wheel-running combined with treated yeast.
2. MPTP-induced hypokinesia was after L-dopa-stimulation partially restored by daily exercise, which effect was increased through wheel-running combined with treated yeast.
3. The MPTP-induced DA depletion at a high dose (2*40 mg/kg) was partially brought back by daily exercise but a combination of wheel-running and treated yeast did not visibly increase the restorative effect.

In the spontaneous-activity test, six-weeks of wheel-running increased significantly locomotion, but not rearing and total activity, for the mice treated with low-dose MPTP during both the 0-20 min and 20-40 test periods in the activity test chambers. The combination of wheel-running and treated yeast, twice a week over a six-week period, increased manifestly the motor activity of MPTP-treated mice over all 3 parameters. According to non-limiting theory of the inventors, the treated yeast are continuing the generation of oscillations after entering the subject of treatment. When the treated yeast contacts the cells of the subject, they are believed to attract each other and connect because of dipole-dipole forces between them. On the membranes of cells from the subject of treatment, lacking electric symmetry, substructures may be formed which in turn form EHF electric fields. The cells with disturbed functions and the externally stimulated cell may, upon contact, form a temporary united system where recovery processes may occur. Such processes are analogous to those occurring in cells with disturbed functions, but since the cell injected into the organism from the outside possesses considerable EHF energy, the exchange of energy between such cell and the cell requiring recovery leads to the enrichment of the latter with the EHF energy so that its recovery is accelerated. After recovery the corresponding cell of the organism becomes symmetric. Interaction between such cell and externally treated cells discontinues and consequently, the extraction of EHF energy from the externally treated cells stops.

The severe functional deficits in mice treated with high-dose MPTP and then subjected to L-Dopa-stimulation were restored by wheel-running; the restorative effect of exercise alone was incomplete, as opposed to that brought about by a combination of exercise and treated yeast. The activity deficits building up from high-dose MPTP excluded rearing (FIG. 4); yet, behaviors in forms of locomotion and total activity following sub threshold dose of L-dopa were completely restored by a 6-week period of wheel-running.

Figure 5A:
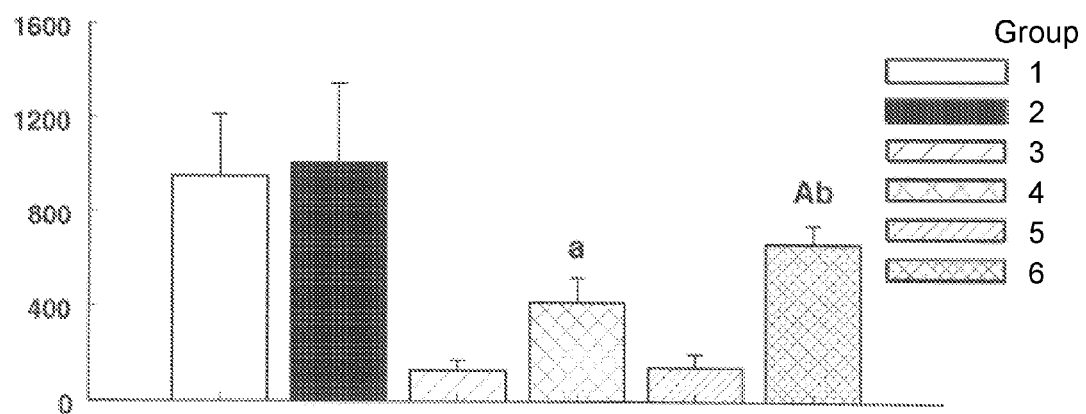
FIG. 5 are diagrams showing mean and SD values for locomotion, rearing and total activity respectively.
Figure 5B:
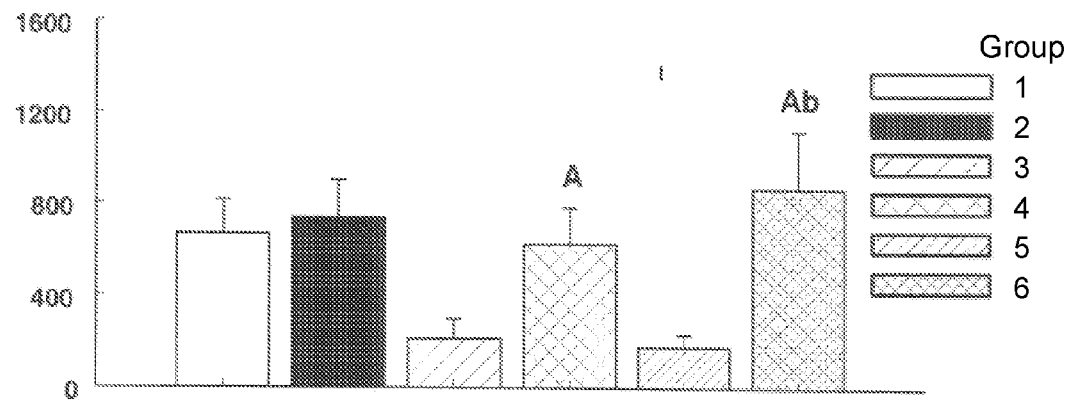
Figure 5C:
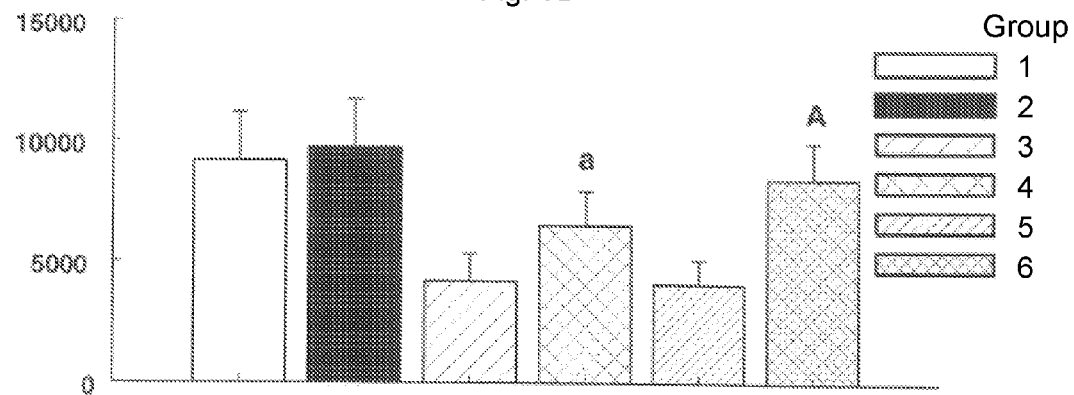

FIG. 5 are diagrams showing mean and SD values for locomotion (FIG. 5A), rearing (FIG. 5B) and total activity (FIG. 5C) respectively, 3 hrs after L-Dopa administration. Treated yeast gives a significant addition of locomotion and rearing in combination with exercise. Letters (uppercase 0.01 and lower case 0.05) indicate significant differences, where A represents comparison between exercise and non-exercise and B, between groups treated with treated yeast.

Treated yeast may also have an effect on the progression of neurodegenerative diseases or disorders, with or without combination with exercise.

Further Experiments

Recovery Study 1

Figure 6A:
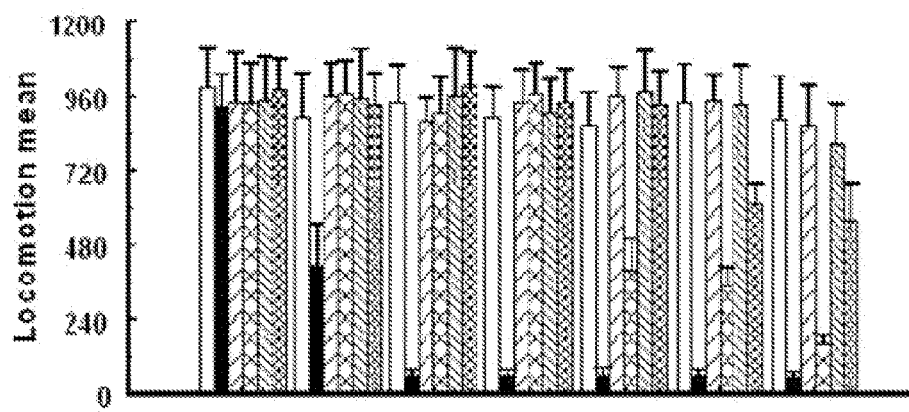
FIGS. 6 to 15 are diagrams showing different results of studies.
Figure 6B:
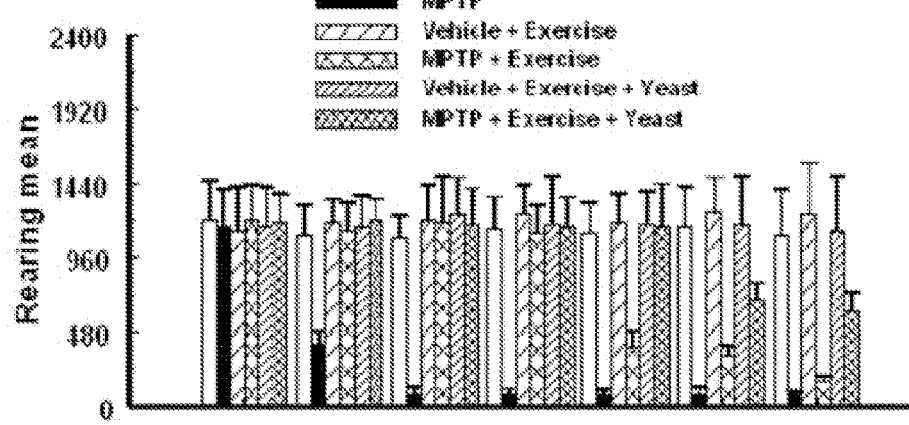
Figure 6C:
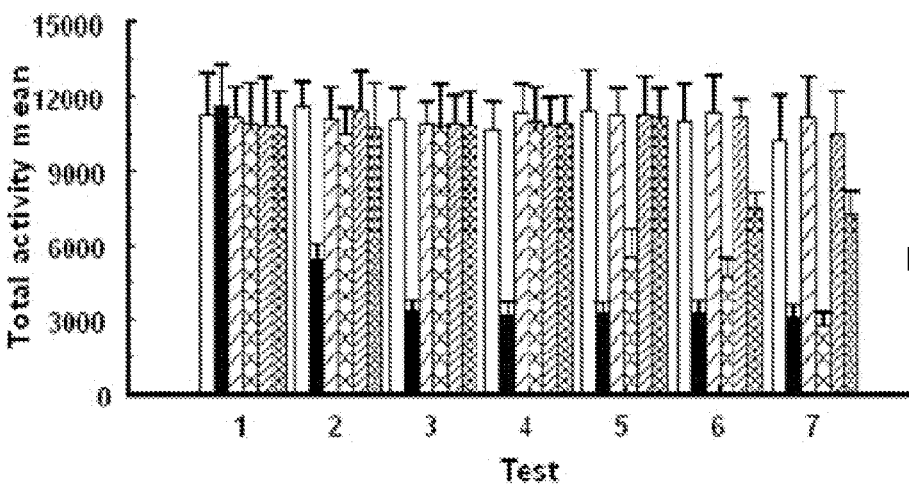

FIG. 6 shows spontaneous motor activity. Exercise regime attenuated the motor activity deficit of MPTP. Treated yeast (yeast) induced almost complete recovery of spontaneous activity.

Figure 7A:
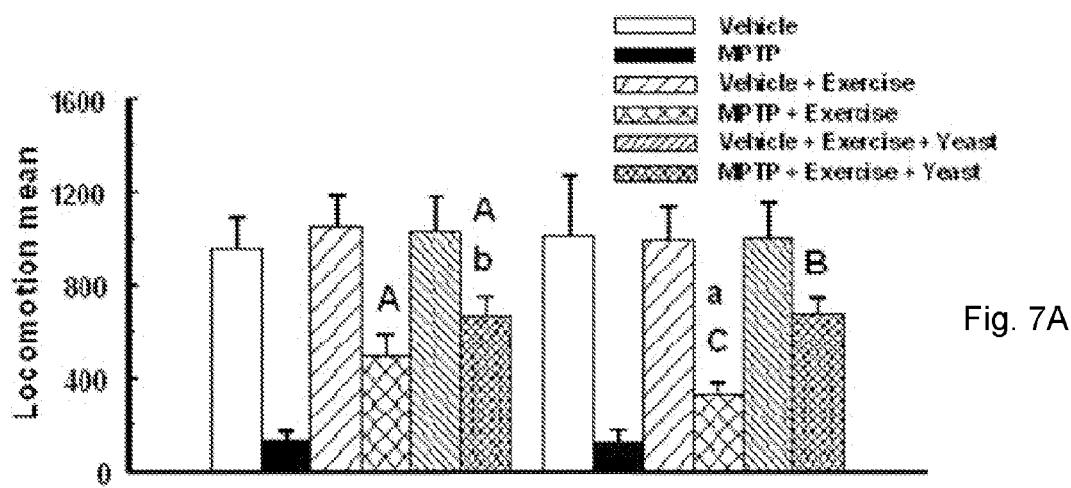
Figure 7B:
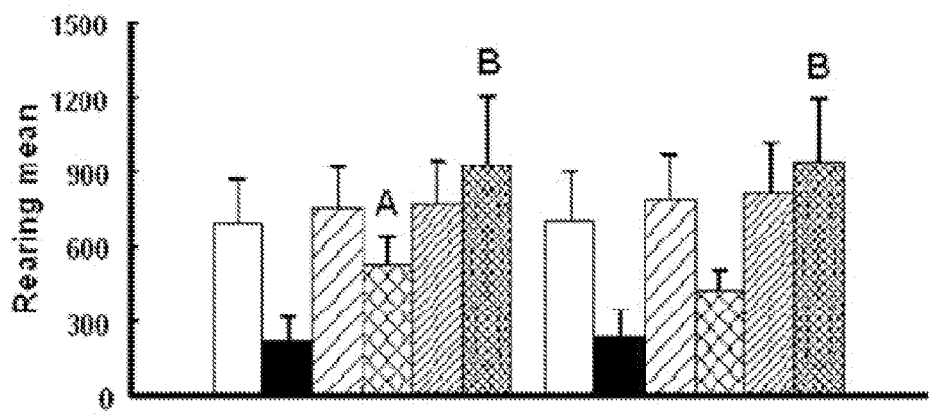
Figure 7C:
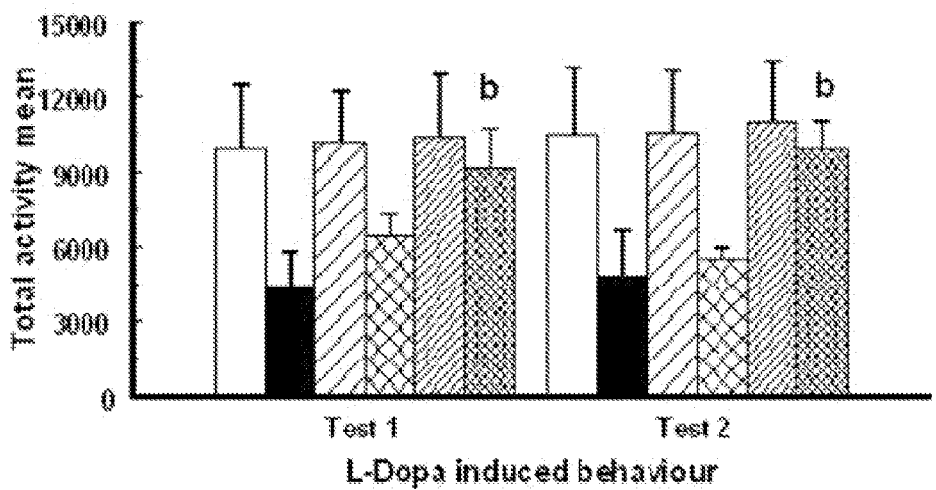

FIG. 7 shows L-Dopa-induced activity. Exercise regime attenuated the motor activity deficit of MPTP. Treated yeast (yeast) induced almost complete recovery of L-Dopa-induced activity.

Figure 8:
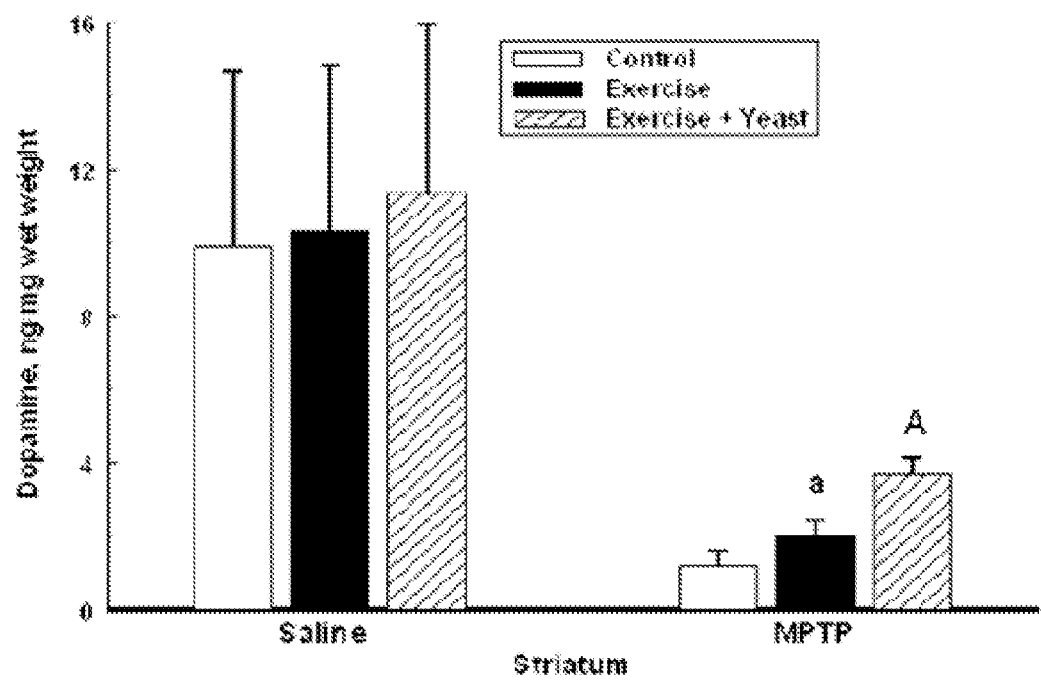

FIG. 8 shows the results of the dopamine analysis. There was a marked recovery of dopamine level in the group treated with Treated yeast (yeast).

Recovery Study 2

Figure 9A:
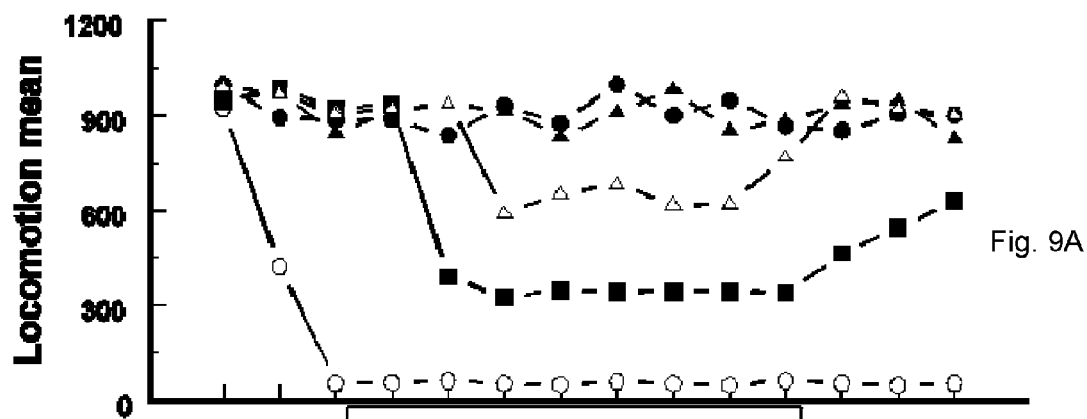
Figure 9B:
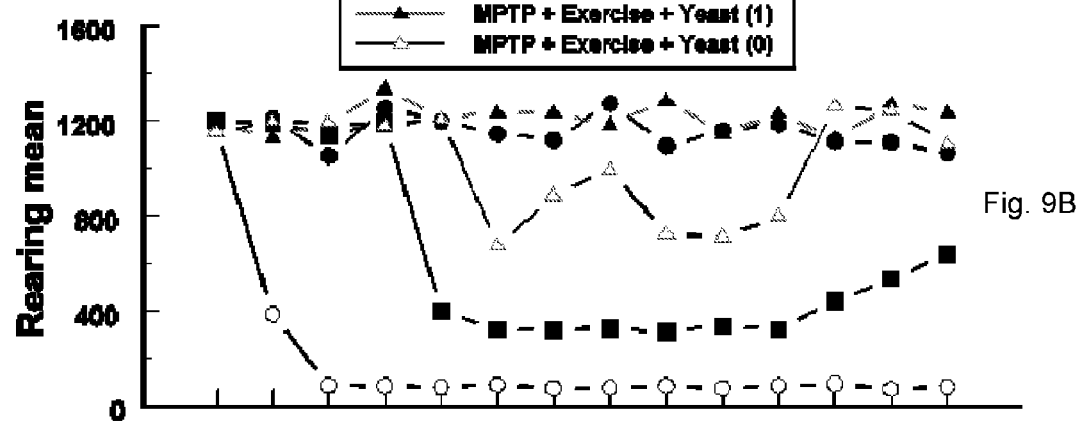
Figure 9C:
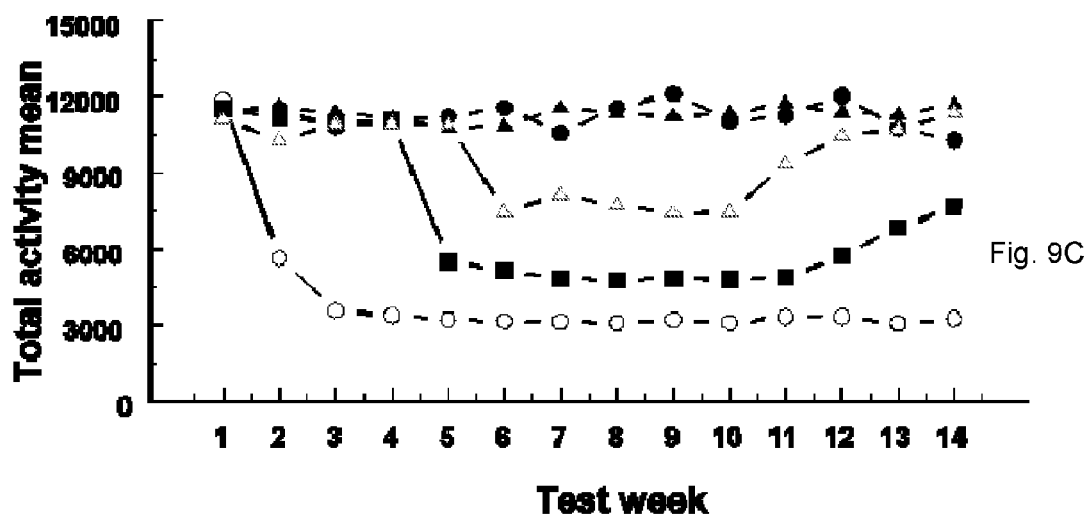

FIG. 9 shows the results regarding spontaneous motor activity. Exercise regime attenuated the motor activity deficit of MPTP. Treated yeast (yeast) induced complete recovery of spontaneous activity.

Figures 10A, 10B, 10C:
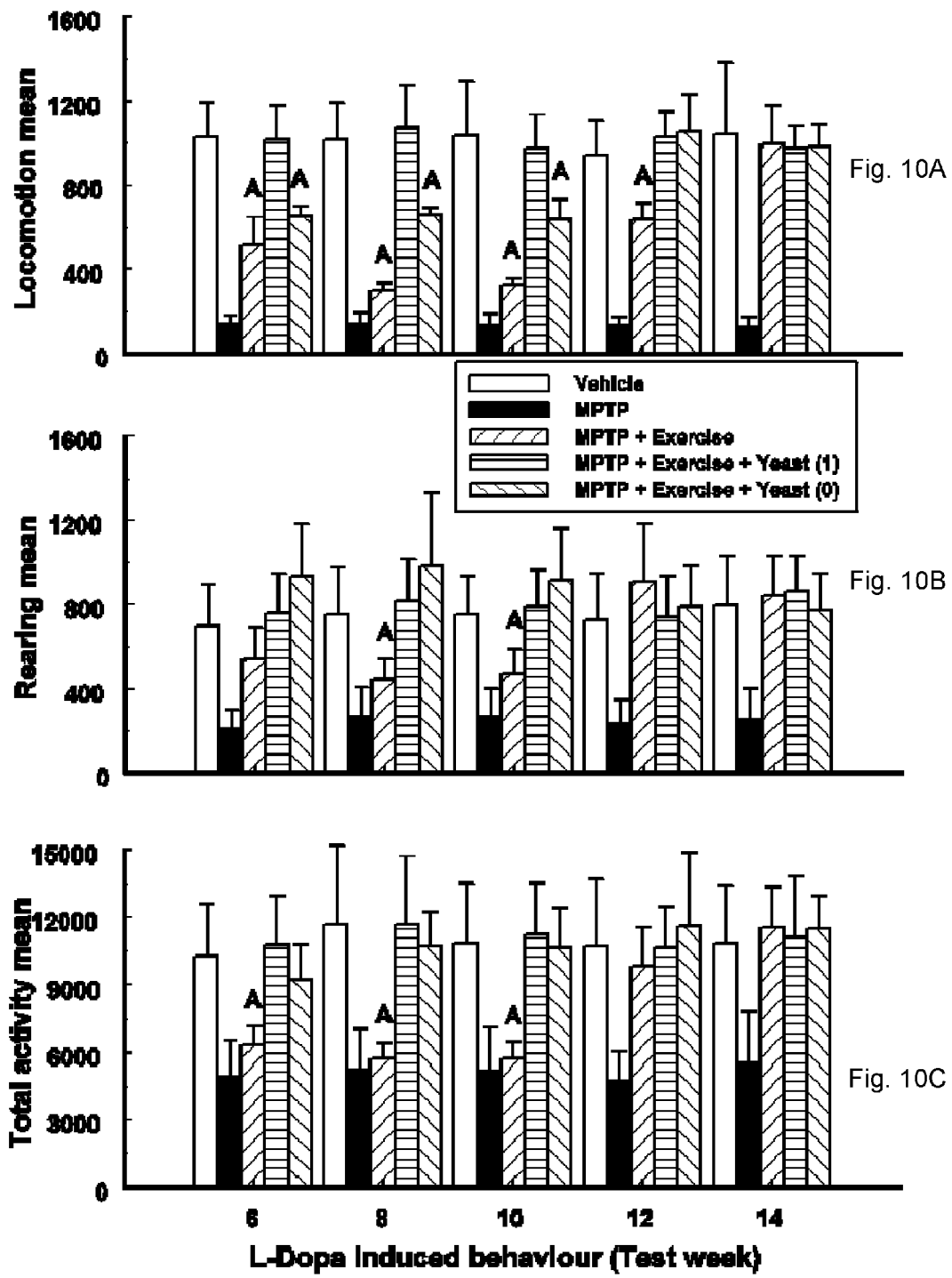

FIG. 10 shows the L-Dopa-induced activity. Treated yeast (yeast) gave complete recovery of L-Dopa-induced activity.

Figure 11:
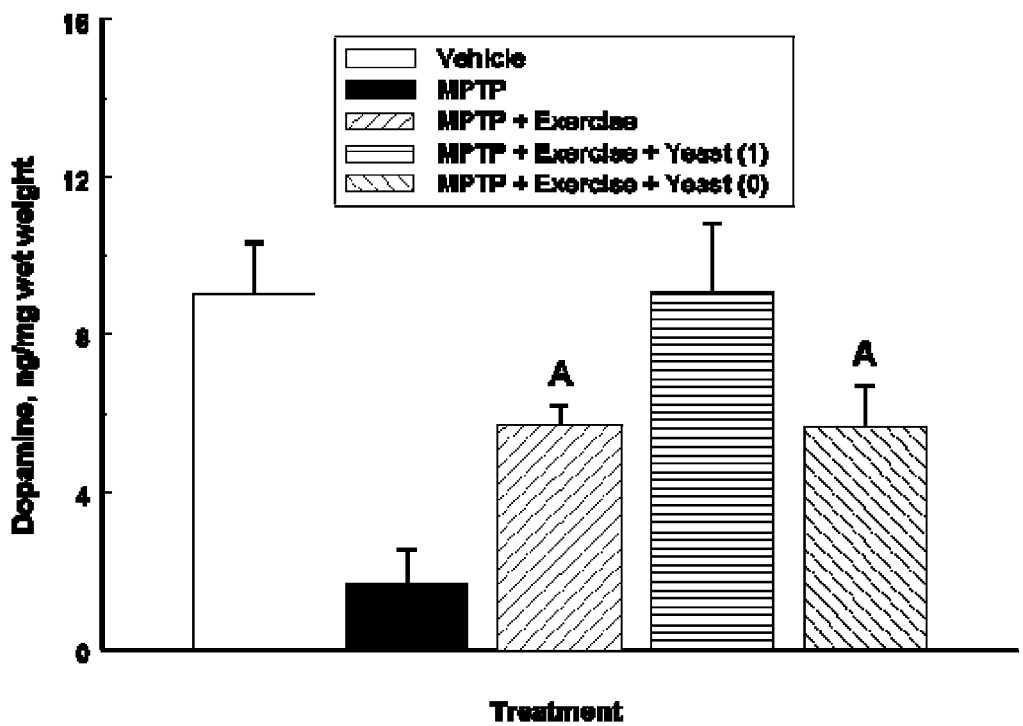

FIG. 11 shows the results of the dopamine analysis. Treated yeast (yeast (1)) gave complete recovery of dopamine level in the mouse striatum.

Figure 12:
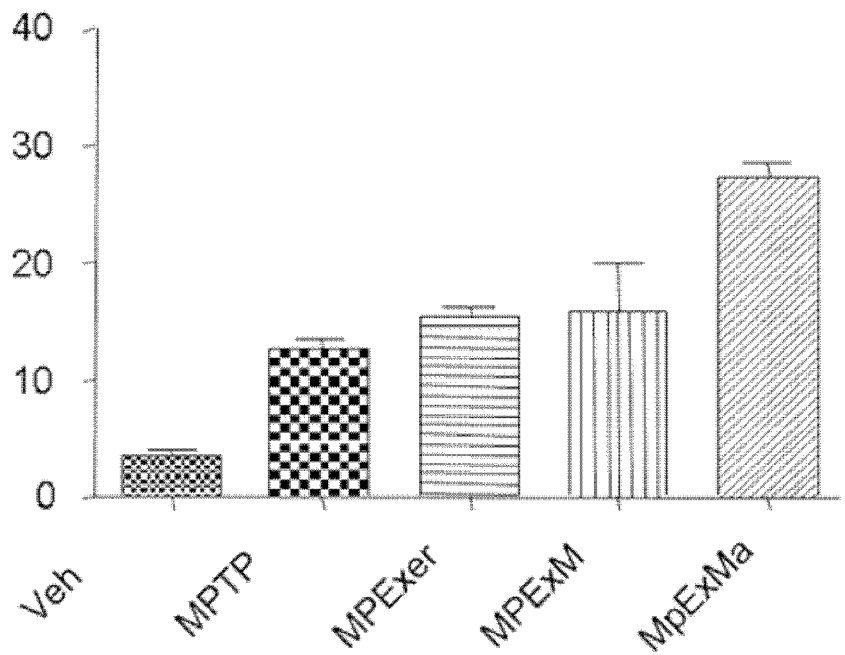

FIG. 12 shows the results of the BDNF analysis. Treated yeast induced a maximal expression of BDNF (MpExMa group) compared with the exercise only (MPExer) and untreated yeast (MPExM) groups. (MpExMa group>MPExM, MPExer groups>MPTP group).

Restoration Study

Figures 13A, 13B, 13C:
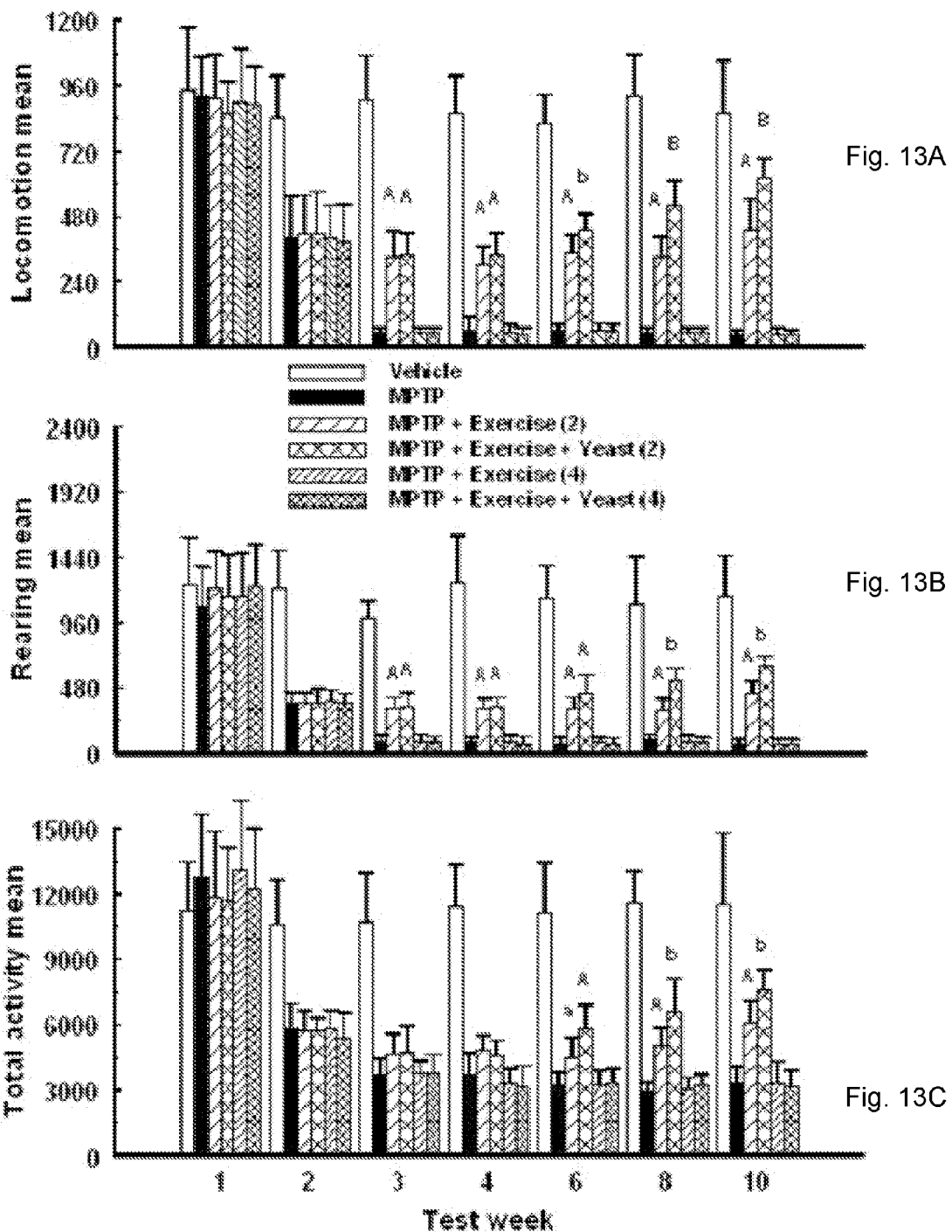

FIG. 13 shows spontaneous motor activity. Treated yeast (yeast) induced marked restorative effects on spontaneous activity after 2 administrations of MPTP.

Figure 14A:
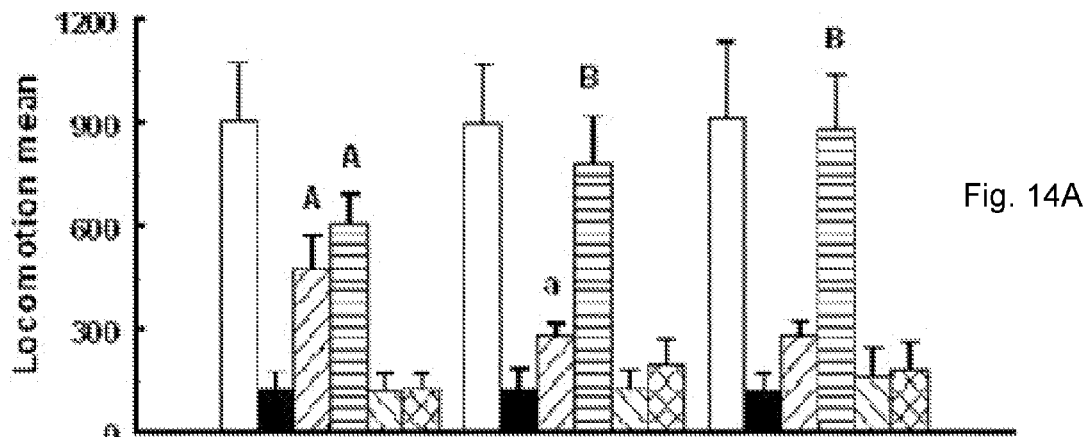
Figure 14B:
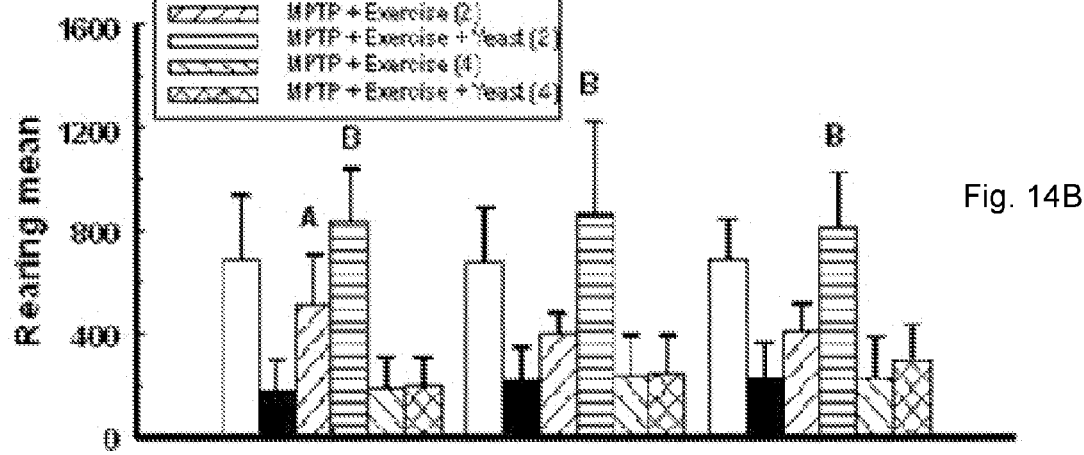
Figure 14C:
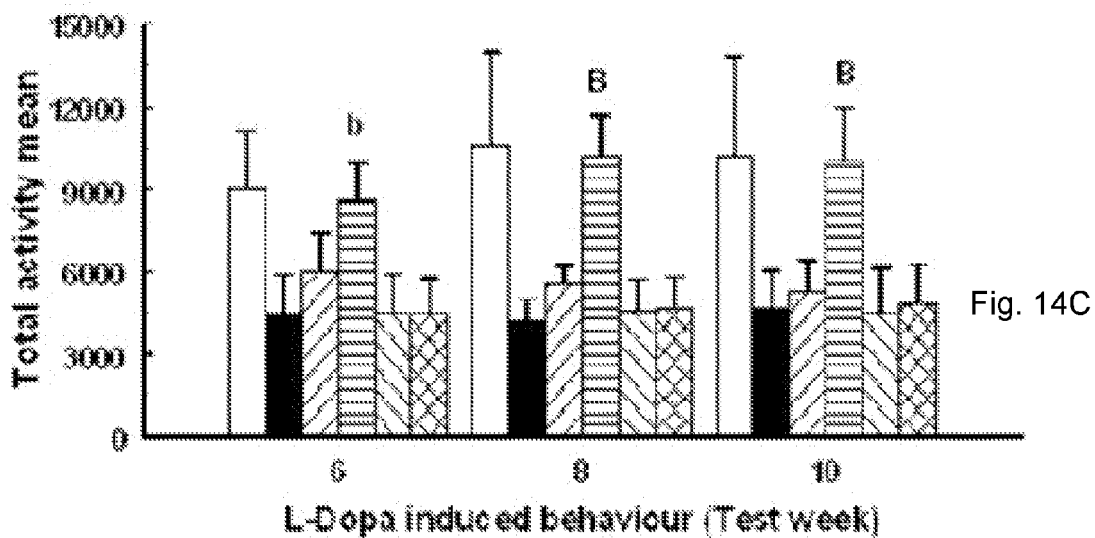

FIG. 14 shows the L-Dopa-induced activity. Treated yeast (yeast) induced complete restorative effects on L-Dopa-induced activity after 2 administrations of MPTP.

Figure 15:
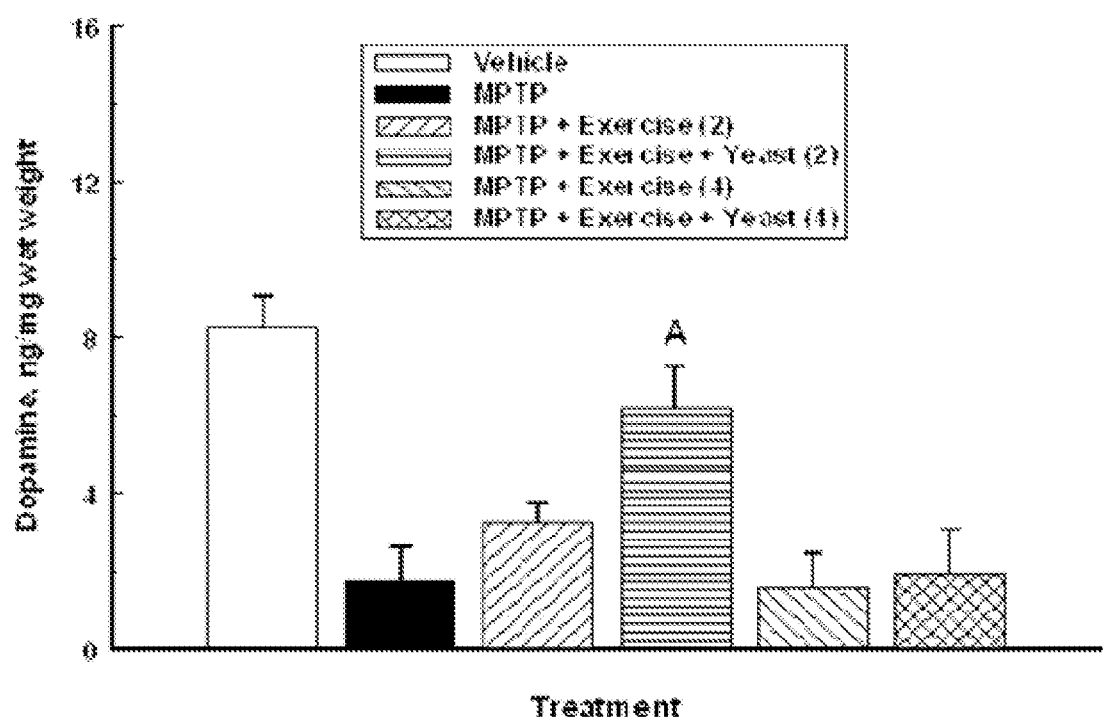

FIG. 15 shows the results of the dopamine analysis. Treated yeast (yeast) induced marked restorative effects on dopamine level after 2 administrations of MPTP.

In the claims, the term "comprises/comprising" does not exclude the presence of other elements or steps. Furthermore, although individually listed, a plurality of means, elements or method steps may be implemented by e.g. a single unit.

Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A method of treatment of a neurodegenerative disease or disorder, comprising administering yeast cells treated with or grown from yeast cells treated with electromagnetic waves in the range of 42.0 GHz to 55.0 GHz, for the treatment or prevention of a neurodegenerative disease or disorder, wherein the disease or disorder is Parkinson's disease.

2. The method according to claim 1, wherein said electromagnetic waves have a power density below 1 mW/cm$^2$.

3. The method according to claim 2, wherein said electromagnetic waves have a power density between 0.004 mW/cm$^2$ and 0.2 mW/cm$^2$.

4. The method according to claim 1, wherein said electromagnetic waves are modulated in a frequency within the range of 0% to about 0.5% of the average frequency.

5. The method according to claim 1, wherein the treatment time is between 20 minutes and 130 minutes.

6. The method according to claim 1, wherein said yeast cells are *Sacharomyces*.

7. The method according to claim 6, wherein said yeast cells are selected from *Sacharomyces carlsbergesis* and *Sacharomyces cerevisiae*.

8. The method according to claim 1, wherein said treatment is oral treatment.

* * * * *